(12) United States Patent
Chaudhri et al.

(10) Patent No.: US 10,176,541 B2
(45) Date of Patent: Jan. 8, 2019

(54) MEDICAL INFORMATION NAVIGATION ENGINE (MINE) SYSTEM

(75) Inventors: Imran N. Chaudhri, Potomac, MD (US); Shahram Shawn Dastmalchi, San Ramon, CA (US); Robert Derward Rogers, Pleasanton, CA (US); Vishnuvyas Sethumadhavan, Mountain View, CA (US); Shamshad Alam Ansari, Fairfax, VA (US); Nikolai N. Kalnine, Belmont, CA (US)

(73) Assignee: APIXIO, INC., San Mateo, CA (US)

( * ) Notice: Subject to any disclaimer, the term of this patent is extended or adjusted under 35 U.S.C. 154(b) by 300 days.

(21) Appl. No.: 13/223,228

(22) Filed: Aug. 31, 2011

(65) Prior Publication Data

US 2012/0060216 A1 Mar. 8, 2012

Related U.S. Application Data

(60) Provisional application No. 61/379,228, filed on Sep. 1, 2010.

(51) Int. Cl.
| | |
|---|---|
| *G06Q 50/22* | (2018.01) |
| *G06Q 50/24* | (2012.01) |
| *G06Q 10/10* | (2012.01) |
| *G16H 10/60* | (2018.01) |

(52) U.S. Cl.
CPC ............ *G06Q 50/22* (2013.01); *G06Q 10/10* (2013.01); *G06Q 50/24* (2013.01); *G16H 10/60* (2018.01)

(58) Field of Classification Search
CPC ...... G06F 19/30; G06F 19/323; G06F 19/324; G06F 19/326; G06F 17/30864;
(Continued)

(56) References Cited

U.S. PATENT DOCUMENTS

| | | |
|---|---|---|
| 7,321,861 B1 | 1/2008 | Oon |
| 2005/0138017 A1 | 6/2005 | Keen et al. |

(Continued)

FOREIGN PATENT DOCUMENTS

| | | |
|---|---|---|
| KR | 10-2009-0050881 | 5/2009 |

OTHER PUBLICATIONS

Lemeshow et al, Searching one or two databases was insufficient for meta-analysis of observational studies, 7 pages (Year: 2005).*

(Continued)

*Primary Examiner* — Hadi S Armouche
*Assistant Examiner* — Huan V Doan
(74) *Attorney, Agent, or Firm* — Kang S. Lim

(57) ABSTRACT

A method of transacting medical information includes receiving medical information from a medical sources, identifying, mapping, and consolidating the received medical information by a back-end medical processor, providing access to specific relevant data, based on a user's security privileges, within the identified, mapped, and consolidated medical information, based on user-specific functions or roles by a front-end medical processor, and generating user-customized processed medical information to a plurality of users, with at least a portion of the user-customized processed medical information being provided to each of the plurality of users based on its relevancy to each user's specific function or role and each user's associated security privileges.

35 Claims, 17 Drawing Sheets

(58) Field of Classification Search
CPC ........ G06Q 50/24; G06Q 50/22; G06Q 10/10; G16H 10/60
USPC ............ 345/501; 382/128; 600/407; 702/19; 705/2, 3, 50; 706/50; 726/5, 21
See application file for complete search history.

(56) References Cited

U.S. PATENT DOCUMENTS

| | | |
|---|---|---|
| 2006/0036619 A1* | 2/2006 | Fuerst et al. .................. 707/100 |
| 2006/0047669 A1* | 3/2006 | Durrence et al. ............... 707/10 |
| 2006/0129435 A1 | 6/2006 | Smitherman et al. |
| 2007/0016450 A1 | 1/2007 | Bhora et al. |
| 2008/0091633 A1* | 4/2008 | Rappaport et al. ............. 706/50 |
| 2008/0263048 A1 | 10/2008 | Wise |
| 2008/0270340 A1* | 10/2008 | Abrams et al. ................... 707/1 |
| 2009/0024615 A1* | 1/2009 | Pedro et al. ....................... 707/5 |
| 2009/0070103 A1* | 3/2009 | Beggelman et al. ............. 704/9 |
| 2009/0112882 A1* | 4/2009 | Maresh et al. .................. 707/10 |
| 2009/0136102 A1* | 5/2009 | Kimpe et al. .................. 382/128 |
| 2009/0271221 A1* | 10/2009 | Aridi et al. ....................... 705/3 |
| 2010/0179827 A1 | 7/2010 | McCallie, Jr. et al. |
| 2010/0185496 A1* | 7/2010 | Hahn et al. ..................... 705/10 |

OTHER PUBLICATIONS

Korean Intellectual Property Office, ISA, "International Search Report and Written Opinion" in PCT Application No. PCT/US2012/053182, dated Mar. 18, 2013, 12 pages.

* cited by examiner

Semantic search examples
Patient: *Joan Sample*

APIXIO™  [Joan Sample x]  [Search 🔍]  [Finish ✉]

- Patient Information
- Labs
- Office Notes
- Medications
- Allergies
- Problems
- Procedures
- Immunizations

Patient Information　　　　　Find additional matches

Name:　　　Joan Sample　　　　　　　　　①
DOB:　　　　01/02/1930
Sex:　　　　F
Update Care Team

Labs

05/18/2010

| | | |
|---|---|---|
| Albumin | 4.1 | 3.6-5.1 |
| Alkaline Phosphatase | H 155 | 33-130 U/L |
| ALT | 30 | 6-40 U/L |
| AST | 28 | 10-35 U/L |
| Bilirubin | 4 | 0.2-12 mg/dL |
| Calcium | 10 | 8.6-10.2 mg/dL |
| Carbon Dioxide | 30 | 21-33 mmol/L |
| Chloride | 104 | 98-110 mmol/L |
| Creatinine | 1.01 | 0.63-1.22 mg/dL |
| eGFR | L 52 | >=60->=60 mL/min |
| Glucose | 91 | 65-99 mg/dL |
| Potassium | 4.1 | 3.5-5.3 mmol/L |
| Protein | 6.3 | 6.2-8.3 g/dL |
| Sodium | 140 | 135-146 mmgl/L |

Relevancy matrix:

| | Chest pain |
|---|---|
| Glucose | 1.0 |
| Creatinine | 1.0 |
| Calcium | 0.0 |
| Sodium | 1.0 |
| Potassium | 1.0 |
| Carbon dioxide | 1.0 |
| Chloride | 0.0 |

FIG. 10

APIXIO™

| | |
|---|---|
| Patient Information | |
| Labs | 63 |
| Office Notes | 7 |
| Medications | |
| Allergies | |
| Problems | 1 |
| Procedures | |
| Immunizations | |

| Joan Sample × | chest pain | Search 🔍 | Finish ✉ |

Patient Information                               Find additional matches (1)

Name:       Joan Sample
DOB:        01/02/1930
Sex:        F
Update Care Team

Labs

05/18/2010

| | | |
|---|---|---|
| Calcium | 10 | 8.6-10.2 mg/dL |
| Carbon Dioxide | 30 | 21-33 mmol/L |
| Chloride | 104 | 98-110 mmol/L |
| Creatinine | 1.01 | 0.63-1.22 mg/dL |
| eGFR | L 52 | >=60->=60 mL/min |
| Glucose | 91 | 65-99 mg/dL |
| Potassium | 4.1 | 3.5-5.3 mmol/L |

FIG. 11

| 📱 Medications | 📶▽📶 |
|---|---|
| Vytorin 10/20 (ezetimibe 10 MG / Simvastatin 20 MG Oral Tablet) | (22) |
| Aciphex 20 MG Enteric Coated Tablet (Rabeprazole sodium) | (3) |
| Master | Merged |

|  |  | all \| none |
|---|---|---|
| ⊙ | Aciphex 20 MG Enteric Coated Tablet (Rabeprazole sodium)<br>code_name: xyz alpha 1<br>param_2:   abc beta 1<br>Param 3:    alpha | ☑ |
| ○ | Aciphex 20 MG Enteric Coated Tablet (Rabeprazole sodium)<br>code_name: xyz alpha 1<br>param_2:   abc beta 1<br>Param 3:    alpha omega | ☐ |

[ Cancel ]   [ OK ]

FIG. 21

MEDICAL INFORMATION NAVIGATION ENGINE (MINE) SYSTEM

CROSS REFERENCE TO RELATED APPLICATIONS

This application claims priority to U.S. Patent Application No. 61/379,228, by Ansari et al., entitled "MEDICAL INFORMATION NAVIGATION ENGINE (MINE) SYSTEM", filed on Sep. 1, 2010.

BACKGROUND OF THE INVENTION

Field of the Invention

The invention relates generally to medical information engine, and particularly to management and consolidation of medical information.

Description of the Prior Art

Despite rapid growth of innovation in other fields in recent decades, the world of medical information, including patient medical records, billing, and a host of other information, has enjoyed little to no useful consolidation, reliability, or ease-of-access, leaving medical professionals, hospitals, clinics, and even insurance companies with many issues, such as unreliability of medical information, uncertainty of diagnosis, lack of standard, and a slew of other related problems.

One of the challenges facing those in the medical or related areas is the number of sources of information, the great amount of information from each source, and consolidation of such information in a manner that renders it meaningful and useful to those in the field in addition to patients. Obviously, this has contributed to increased medical costs and is perhaps largely attributed to the field suffering from an organized solution to better aid the medical professionals, to better aid those requiring more reliable patient history and those requiring more control and access over such information.

Currently, when a patient sees various medical professionals over the years, there is no method for universally tracking recommendations, thoughts, prescriptions, diagnosis. This hinders the job of insurance companies in making certain requisite determinations, physicians making decisions that directly impact the health of the patient, and hospitals and other medical institutions who similarly rely but do not have the benefit of the requisite information, not to mention the patient.

Further, there are problems in the current medical system that are associated with patient identity in that due to the exposure of a patient to various medical associations/professionals over the years and the possibility of various ways of identifying the same patient, patients' records and identity are oftentimes compromised, creating a slew of problems both for the patient as well as those treating the patient.

Further, privacy of a patient's health records is not currently reliably maintained, as there are too many cases of health record compromises. Additionally, patient control of access to medical information is nearly nonexistent. Additionally, secure and remote access of medical information is currently lacking.

Therefore, what is needed is a method and apparatus for managing medical information in a manner that is beneficial, reliable, portable, flexible, and efficiently usable to those in the medical field, including patients.

SUMMARY OF THE INVENTION

To overcome the limitations in the prior art described above, and to overcome other limitations that will become apparent upon reading and understanding the present specification, the present invention discloses a method and a corresponding structure for transacting medical information.

Briefly, a method of transacting medical information is disclosed to include receiving medical information from a medical sources, identifying, mapping, and consolidating the received medical information by a back-end medical processor, presenting access to specific relevant data, based on a user's security privileges, within the identified, mapped, and consolidated medical information, based on user-specific functions or roles by a front-end medical processor, and generating user-customized processed medical information to a plurality of users, with at least a portion of the user-customize processed medical information being provided to each of the plurality of users based on its relevancy to each user's specific function or role and each user's associated security privileges.

These and other objects and advantages of the invention will no doubt become apparent to those skilled in the art after having read the following detailed description of the preferred embodiments illustrated in the several figures of the drawing.

IN THE DRAWINGS

FIGS. 10-19 show various screen shots of search results, in accordance with exemplary embodiments of the invention.

FIG. 21 shows a computer display or screen shot of reconciled data, in accordance with an exemplary output processed by the visualizer 438.

DETAILED DESCRIPTION OF THE PREFERRED EMBODIMENT

In the following description of the embodiments, reference is made to the accompanying drawings that form a part hereof, and in which is shown by way of illustration of the specific embodiments in which the invention may be practiced. It is to be understood that other embodiments may be utilized because structural changes may be made without departing from the scope of the invention.

Figure 1:
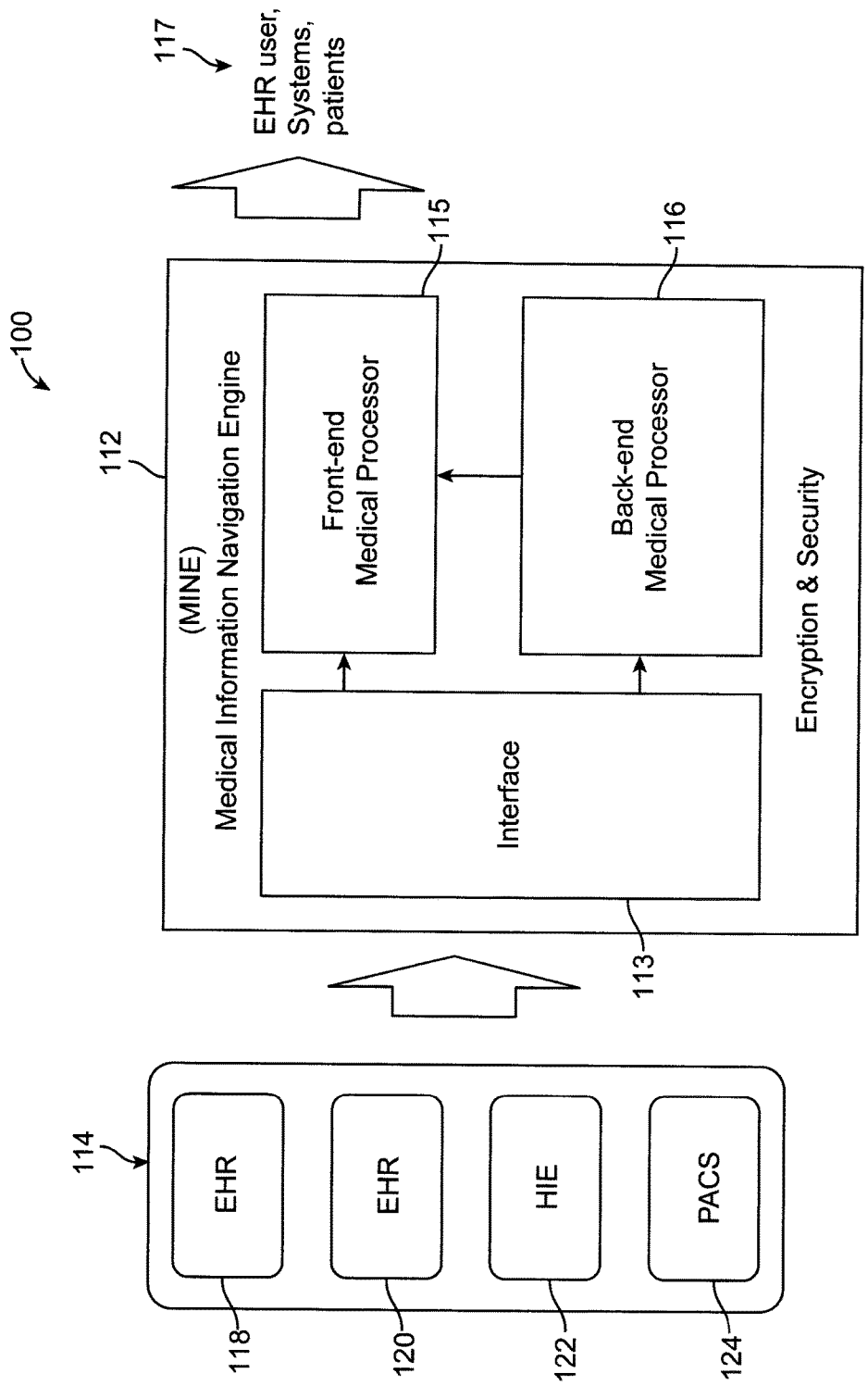
FIG. 1 shows a medical system 100, in accordance with an embodiment of the invention.

Referring now to FIG. 1, medical system 100, in accordance with an embodiment of the invention. The system 100 is shown to include medical source 114, a medical information navigation engine (MINE) 112, and medical information consumers (also referred to herein as "output" or "medical output") 117. The medical source 114 are shown to include an electronic health record (EHR) 118, EHR 120, health information exchange (HIE) 122, and a picture archiving and communication system (PACS) 124. The MINE 112 is shown to include interface 113, a back-end medical processor 116, and a front-end medical processor 115.

"Medical information", as used herein, refers to any health-related information, including but not limited to patient medical records, patient entered information, care team entered information, healthcare device generated information, and billing information.

The source 114 generally provides various medical information to the MINE 112. For example, the EHRs 118 and 120 each may provide information such as medical records and billing, the HIE 122 may provide information such as medical records, and the PACS 124 may provide information such as diagnostic imaging and reports.

The medical information consumers 117, which may be made of a host of entities or individuals, such as patients, clinics, medical institutions, health organization, and any other medical-related party, use information that is provided by the processor 115 of MINE 112 and that can, by way of example, consist of patients, medical systems, medical organization administrators, medical researchers, and/or EHR users. For example, user-customized processed medical information is provided by the processor 115 to a number of users within the medical information consumers 117. In this case, the processor 115 generates user-customized processed medical information to a plurality of users, with at least a portion of the user-customize processed medical information being provided to each of the users based on the relevancy of the portion being provided of each user's specific function or role and each user's associated security privileges.

The processor 116, in some embodiments, indexes identifies, maps, and consolidates medical information, received from the interface 113, and tags this information, and determines to reconcile the tagged information. In some methods and embodiments, information that is extracted from images is tagged to enhance recall of search queries. Indexing, at least in part, processes document and converts them into formats that allows for quick searching across a large collection of documents.

The information in the MINE 112 is encrypted and secure to ensure privacy of sensitive medical information.

It is understood that the sources 114 of FIG. 1 includes merely some examples of the sources that communicate with the MINE 112 and that other sources, known to those in the field, are contemplated. Similarly, the output 117 may be used by those or entities not discussed herein but that are contemplated and within the scope and spirit of the invention.

The interface 113 serves to receive information that is in various forms, such as but not limited to text, html, CCD, CCR, HL7 and any other type or formatted information. The interface 113 then provides to the processors 115 and 116 information, as needed.

The processor 116 receives some of the medical information that the interface 113 processes and performs certain tasks to process it, such as indexing, semantic meta-tagging, and reconciliation. Indexing takes processed documents and converts them into formats that make it easy to quickly search across a large collection of documents. Semantic meta-tagging embeds information into the medical information that is relevant thereto and that can be later used to search for certain information for the purpose of reconciliation and search, among many others.

One aspect of consolidation, reconciliation and deduplication, generally refers to removing of redundant patient medical records, such as, multiple records for the same individual appearing as though the records are for different individuals or multiple data elements that are recorded similarly but slightly differently in the different sources. In this case, the processor 116 recognizes that the records belong to a single individual or are the same data and just recorded differently and automatically consolidates them. The patient or a user of the system 100 may also manually perform reconciliation. Whether or not reconciliation is performed is advantageously determined by the processor 116.

The processor 116 outputs the indexed, tagged and reconciled information to the processor 115. The foregoing tasks are a generalization and further details of each are provided below.

The processor 115 performs certain tasks on the information provided by the interface 113 and the processor 116, which include query, search, presentation, and quality checking. The output of the processor 115 is the output of the MINE 112, or output 117.

The MINE 112, through the processor 115, in some embodiments and methods, invites members of a medical care team to join it thereby allowing distributed user-organized care teams.

Querying, as performed by the processor 115, is the ability to receive, as input, a free text query, from a user, (i.e., a query without any restrictions on the structure)—and converting the free text query into commands to a medical search engine, such as Medical Lexical Search Engine and the MATRIX (Medical Application Terminology Relationship IndeX) Concept Search Engine, using a sophisticated query processing engine optimized to work with medical queries. The results of the search engine are sent to the presentation display planner—which decides the most relevant presentation given the user's organization and role (e.g. the provider, search query program, a healthcare administrator, a study administrator, and the patient). The presentation discussed below, receives such information. In some embodiments and methods, the medical information or user information is processed to suggest relevant queries.

Search, as performed by the processor 115, is built around the concept of Zero-Click Relevance—or the ability to get to all the relevant information an actor in the healthcare system requires by typing in just a single query. The search engine, within the processor 115, performing the search comprises an indexing and searching, as will become apparent shortly. Optionally, search results may be securely embedded into third party programs. In some embodiments, searching involves determining presenting (also referred to herein as "providing") access to specific relevant data based on a search query, the patient, and the user's specific function and/or role and security privileges. A user may be within the output 117 and security privileges are either determined by the MINE 112 or by the patient or both. Information, uploaded to the MINE 112, by users, such as output 114, in some embodiments, is searched by the processor 115. The uploaded information may include information such as but not limited to status posts, records, and images. Such user-uploaded information is routed automatically to the output 117, as needed.

Some aspects of the search are now discussed relevant to an example. Assuming, by way of example, that general practitioner Dr. Smith's new patient, Joan Sample, has a complaint of chest pain. Joan has brought several ACCDs and a 600-page pdf file of her chart. She has seen a cardiologist who uses NextGen and a G.I. specialist whose charts are in a e-MDs, and has visited the emergency room. Dr. Smith uses the search of the various methods and embodiments of the invention to efficiently assemble the relevant information he needs. Dr. Smith selects Joan Sample as the patient and enters the clinical context "chest pain" in the search bar of a screen presented by the MINE 112 (examples of such screens are shown in subsequent figures herein). He is presented with relevant lab results, such as CKMB and Amulase, relevant diagnostic results, such as EKG and chest CT scan, and all progress notes and consult reports in which concepts relevant to chest pain, like "GERD" and "Holter monitor", are mentioned. Two distinct types of searches are combined, in accordance with a method and embodiment of the invention, to retrieve information medically relevant to Joan's complaint: 1) Lexical search, where text in the patient record is searched for occurrences of the search term, its variants and synonyms; and 2) Medical concept search, where data that is medically related to the search term is retrieved. Medical concept search finds relevant structured data with standardized codes, such as lab results, and text results, such as progress notes, which include terms medically related to the search term. In Joan's case, a search for "chest pain" returns a CKMB lab result and a reference to a chest CT scan. Accordingly and advantageously, the Lexical and Medical concept search solves Dr. Smiths' information overload problem by returning information in the chart most relevant to Joan's chest pain complaint. Further, in some embodiments, the presentation, discussed shortly, presents a united view of Joan's history by reconciling and de-duplicating data from multiple sources that may be coded and described differently. Redundant data is automatically reconciled even if it is described differently by differently sources.

Presentation, as performed by the processor 115, is displaying health information to the requesting user in a way that reduces the number of clicks and maximizes the amount of meaningful information delivered based on the interpreting the intent of the user query.

Quality checking, as performed by the processor 115, is checking of the quality of medical information provided by various sources, i.e. source 114, by the patients, structured data, and unstructured data, in a Wiki-like mannered setting whereby the users can help maintain and improve the quality of information displayed. The foregoing tasks, performed by the processor 115, are further described in detail below. Additionally, the users or patients may make comments regarding medical information, in a Wiki-like manner.

In summary, the MINE 112 transacts medical information including the interface 113 receiving medical information from a number of medical sources (such as within the source 114) for processing, identifying, mapping, and consolidating by the medical processor 116, providing access to specific relevant data, based on a user's security privileges, within the identified, mapped, and consolidated medical information, based on user-specific functions or roles, performed by the processor 115, and generating user-customized processed medical information to a number of users, such as within the output 117, with at least a portion of the user-customized processed medical information being provided to each of the users based on its relevancy to each user's specific function or role and each user's associated security privileges.

Figure 2:
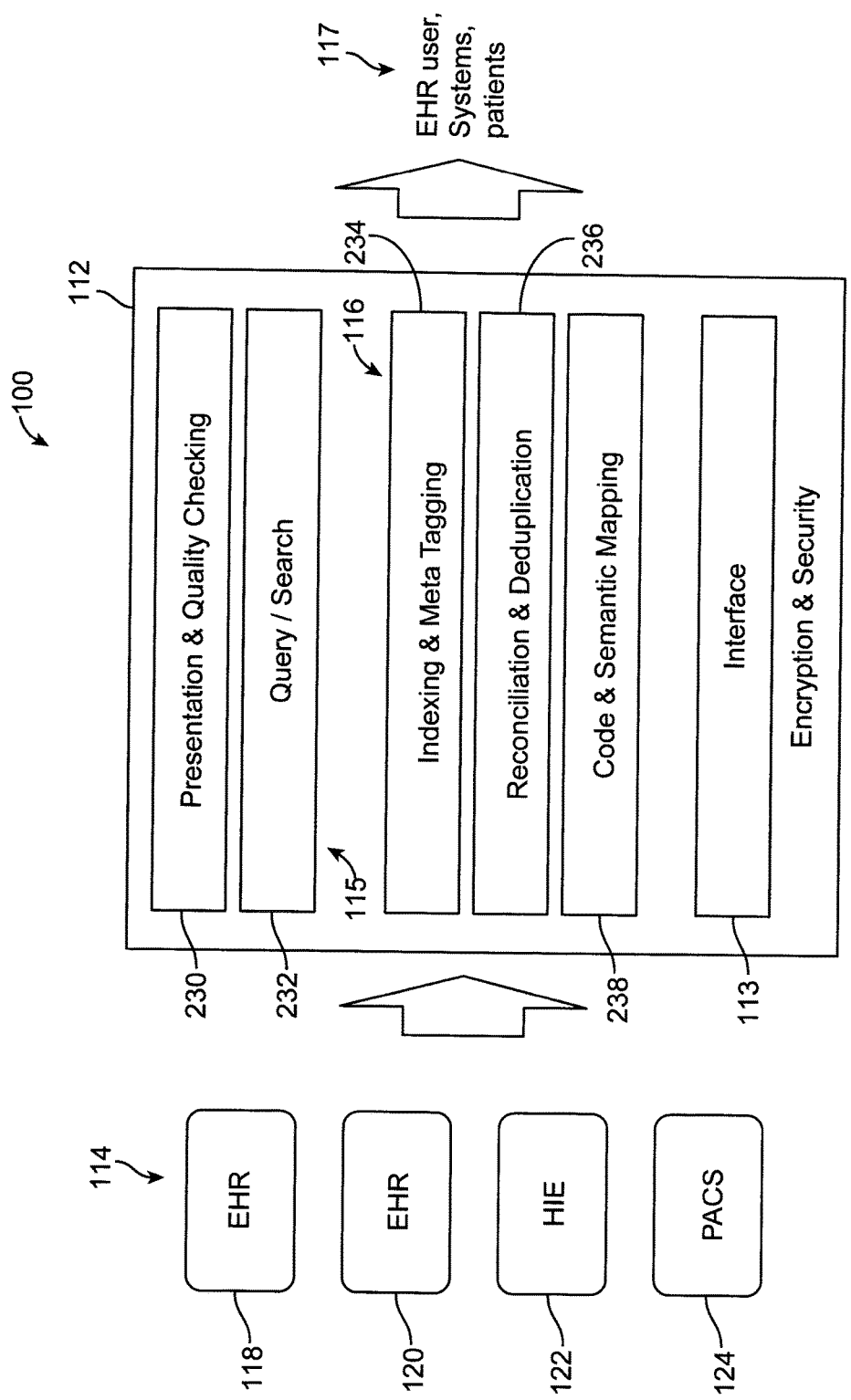
FIG. 2 shows further details of the MINE 112 of FIG. 1, in accordance with an embodiment of the invention.

FIG. 2 shows further details of the system 100, particularly the MINE 112 thereof. That is, the processor 116 is shown to include an indexing and meta tagging module 234, which includes an indexing module and a meta tagging module (both of which are not shown in FIG. 2 in the interest of clarity), which may be a module, as shown in FIG. 2 or two physically separate modules. The processor 116 is further shown to include a reconciliation and de-duplication module 236, which also can be broken out into two modules, a reconciliation module and a de-duplication module, and a code and semantic mapping module 238, which also may be a single module or multiple modules. The modules 234, 236, and 238 communicate with one another.

The processor 115 is shown to include a presentation and quality checking module 230, which may be a single module or broken out into two modules, and a query and search module 232, which also may be separate or combined modules. The modules 230 and 232 communicate with each other and with the modules of the processor 116. The interface 113 communicates with modules of both processors 115 and 116 and is essentially a gateway into the MINE 112 from the sources 114.

The foregoing modules may be software programs, executed by a computer or computing engine of suitable sorts, or may be implemented in hardware.

Figure 3:
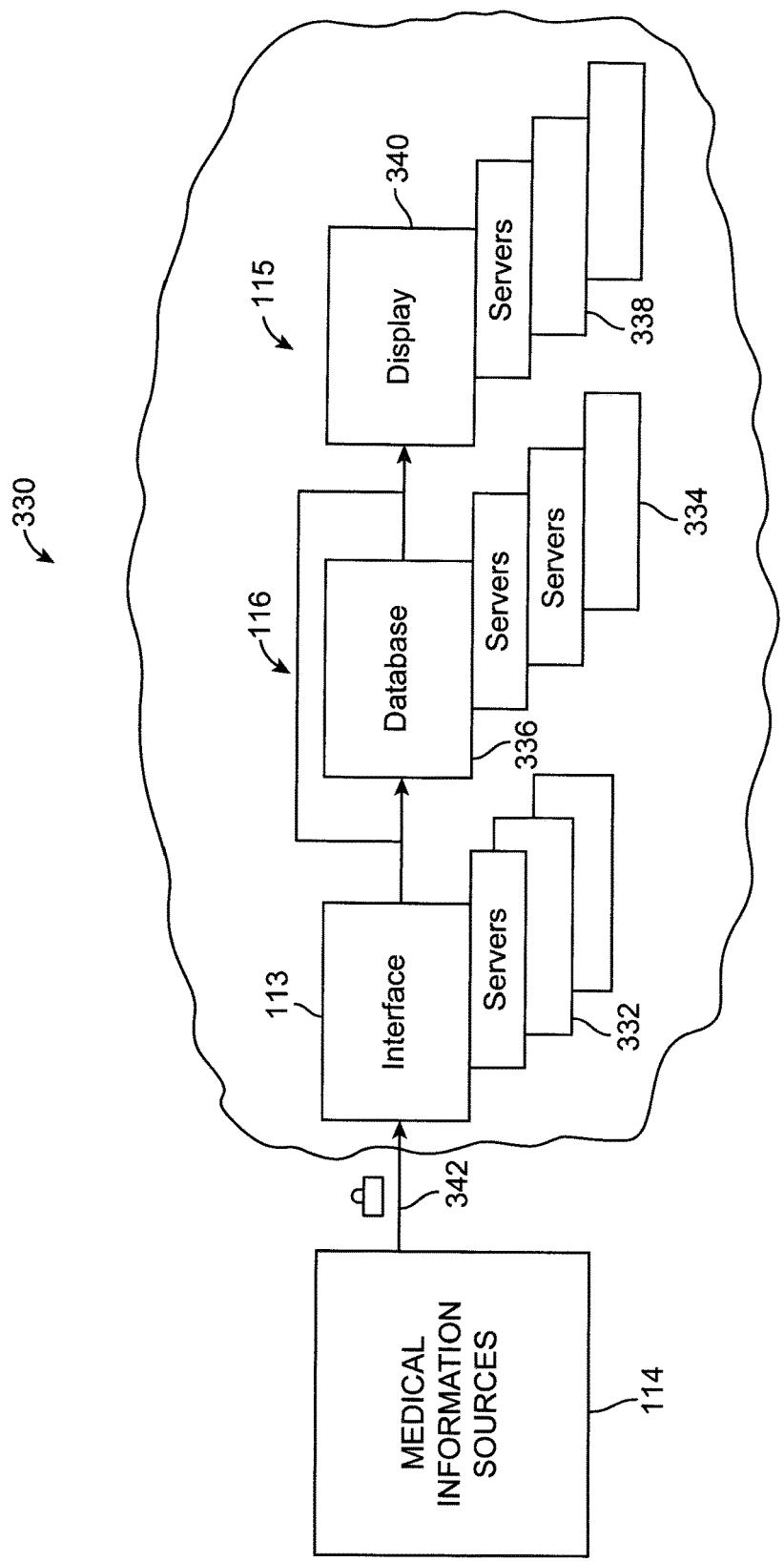
FIG. 3 shows an exemplary embodiment implementing the system 100 using various devices.

FIG. 3 shows an exemplary embodiment implementing the system 100 using various devices. That is, the medical system 330 is analogous to the system 100 and is shown to include the sources 114 coupled to communicate, securely, through the secure communication link 342, to the interface 113. The link 342 may be any suitable communication channel allowing information, of various formats and types, to be transferred to the interface 113 in a secure and encrypted fashion. Exemplary communication channels of which the link 342 is made include the Internet, VPN connections over the Internet, private dedicated digital lines such as T1, T3, E1, E3, SONET, and other fiber optic formats.

The interface 113, in some embodiments, is a software program that executes on one or more servers 332, which can be a server of any kind of suitable computing engine, such as personal computer (PC). The servers 332 receive secure information through the link 342 from the sources 114. The processor 116, in some embodiments, includes a database 336 and one or more servers 334, which may be any suitable computing engine, similar to the servers 332, including but not limited to PCs or servers.

The database 336 and servers 334 perform the tasks discussed above relative to the processor 116 and the display 340 and servers 338 perform the tasks discussed above relative to the processor 115 though these processors may and often perform additional tasks related to medical information, some examples of which are presented and discussed below and the rest of which are contemplated and achieve the various advantages, results and functions presented herein.

The processor 115, in some embodiments, includes display and visualization 40 executing on one or more servers 338, which may be any suitable computing engine, similar to the servers 332, including but not limited to PCs or servers. The display 340 is used to construct presentation and display information to users, such as the patient's records, billing information, and other types of medical information. The display 340, in some embodiments, also performs processing of some of the functions of the processor 115.

As shown in FIG. 3, the servers 332 are coupled to the database 336 and the servers 334, and to the display 340 and the servers 338 and the database 336 and servers 334 are coupled to the display 340 and the servers 338.

In some embodiments, the interface 113, servers 332, database 336, servers 334, display 340, and servers 338 are remotely located relative to the sources 114 and in some embodiments, remotely located relative to one another. Further, they are considered a part of the Internet cloud where, performing their tasks in a manner known as cloud-computing. However, other manner of achieving the functions and advantages of the invention, including various other of implementation, not shown in FIG. 3 or other figures herein and/or not discussed are contemplated.

Figure 4:
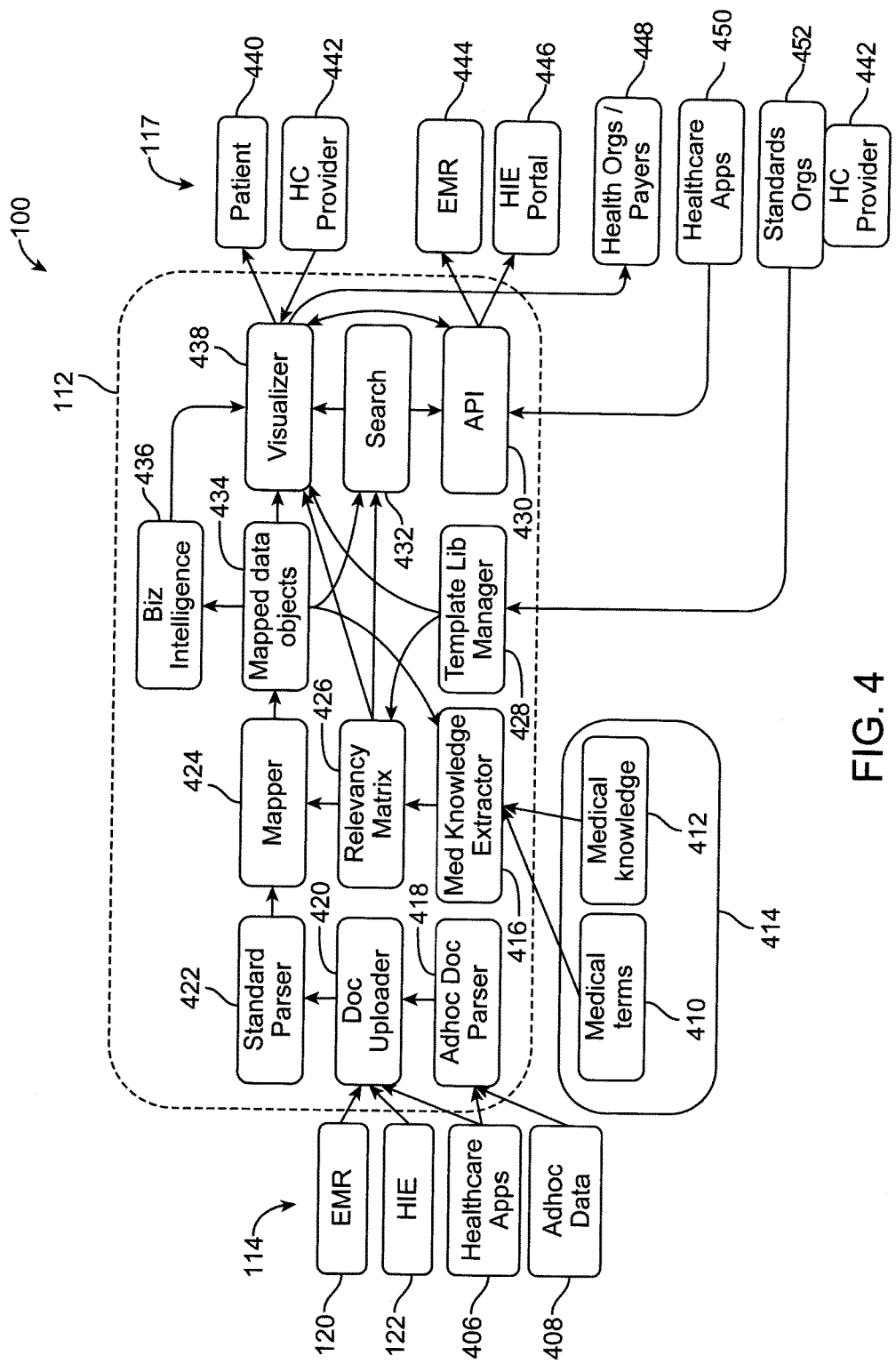
FIG. 4 shows further details of the system 100, in accordance with an embodiment of the invention.

FIG. 4 shows further details of the system 100, in accordance with an embodiment of the invention. The system 100 is a block diagram of thereof with arrows shown linking the blocks to one another. It is understood that these arrows represent data flow between blocks and merely examples of some of the data flows and not all-inclusive thereof.

The system 100 is shown to include medical sources 114, MINE 112, which is analogous to MINE 112 of FIG. 1 with additional details shown, medical output 117, medical source 114, and medical input 414. The source 114 is analogous to the source 114 of FIG. 1 except that it is shown to include electronic medical record 120, HIE 122, healthcare applications 406 and an adhoc data block 408. The output 117 is analogous to the output 117 of FIGS. 1 and 2 except that it is shown to include the patient 440, the health care (HC) provider 442, the EMR 444, the HIE portal 446, healthcare Apps 450, Standards Orgs 452, and Health Orgs/Payers 448. The input 414 is shown to include the medical terms 410 and the medical knowledge 412, which are input to the MINE 112.

The MINE 112 is shown to include a standard parser 422, a document uploader 420, an adhoc document parser 418, a mapper 424, a relevancy matrix 426, a medical knowledge extractor 416, a mapped data objects block 434, a business intelligence block 436, a template library manager block 428, an Application Programming Interface (API) 430, a search module 432, and a visualizer module 438, which are some of the blocks/functions performed by the MINE 112 while others are contemplated to achieve the various functions and advantages discussed herein.

The search module 432 performs functions discussed hereinabove and other functions that will become further clear with subsequent discussions. Similarly, the visualizer module 438 performs the functions discussed above with further details provided in subsequent discussions. The parser 418, the uploader 420, and the parser 422 provide the capability of the MINE 112 to accept information, in a variety of different formats such as a collection of medical records, in standard and ad hoc forms, by the source 114. For example, the adhoc data block 408 may provide information to the MINE 112 in ad hoc form, which the parser 418 decodes or parses for use by other blocks of the MINE 112.

The extractor 416, the matrix 426, and the mapper 424 serve to collectively collect medical knowledge and identify, extract and map multidimensional relationships within them. Multidimensional relationships are between different types of medical data such as concepts, labs, problems, vital, medications, allergies as well as different types of relationships between the medical data such as "has comorbidity with" and "cures" for a drug. These multidimensional relationships are embodied in the relevancy matrix 426. The block 434 serves to combine medical records with their relevancy to specific medical concepts. For example, the specific medical concept of diabetes is related to the labs for hemoglobin a1c and glucose results, to the medical concept of diabetic retinopathy, the diagnosis of foot sores, the medications of Metformin and insulin among other things. The module 438 serves to perform the functions of relevancy and reconciliation and presentation, as described hereinabove. The business intelligence block 436 can mine the collected data for trends and predictive capabilities that might be of interest to large health organizations and payers 448. The collected data can be mined/analyzed/observed/reported on, in aggregate form. Other organizations that could make use of the data are any organizations interested in monitoring or required to report quality metrics such as integrated delivery networks (IDNs), healthplans and/or accountable care organizations (ACO). An example of business intelligence queries includes selecting an arbitrary cohort population for search of quality measures such as "show me all patients' information within my panel with diabetes with hemoglobin a1c high in the last six months".

The sources 114 provides medical information to the MINE 112, through a secure link, as noted previously. Within the medical information received by the MINE 112 generally is medical data or medical records. Before it is received by the MINE 112, medical data is created in a multitude of systems including the EMR 120, healthcare applications 406, and many other ad hoc data sources 408 (such as but not limited to the application, MicroSoft Word). The data, which is typically aggregated in a HIE 122 and EMRs 120 can also be received by MINE 112. Structured data is increasingly becoming available in standard 'xml' formats such as continuity of care records (CCR), continuity of care documents (CCD), clinical data architecture (CDA), and other HL7 related standards. Ad hoc data is available in multiple formats such as word, pdf, fax, and image data. The collection of medical records from multiple sources creates a serious data duplication problem in the current medical environment. Much of the data from these sources may represent the same type of information or even the same instance of information with slightly different variations or completeness (e.g. Patient name with and without the middle initial or a drug labeled as a generic or brand name with or without a start date). The MINE 112 advantageously reconciles the same data instances for reconciliation purposes from different sources and identifies similar data instances for comparison purposes.

As opposed to typical health information exchange (HIE) where patient information is available to all the participants in the system, in the system 100, patient data is shared in a granular patient centric style to accommodate privacy and security on a per patient "need to know" basis based on the roles and needs of the users and their organizations. Examples of the "need to know" basis of information distribution include the following: (1) Some organizations such as those with healthcare providers may receive patient demographics in addition to the other medical information. (2) Other organizations such as sponsors may receive only the problem that the healthcare provider is interested in. (3) Still other organizations, such as study clients may just receive a count of patients that could fit a study candidate criteria and the be able to message those patients anonymously. The whole user interface presented by the presentation module 230 can change based on the rights and type of user. Patient sharing is performed on a patient or even more granular basis. Examples of further granularity include type of data such as labs, meds, allergies, billing data or medical concepts such as mental health and AIDS (PC1). Organizations can share data with each other on an as needed basis this is similar in concept to sending a fax containing medical information for a given patient from one organization to another. The receiving party (organization or healthcare provider 442), health organization/payers 448 in FIG. 4, can accept the sharing (similar to filing the received data into an existing or new patient chart) or reject the sharing request. In this manner, patient care teams are created in an ad hoc distributed way based on care requirements for each particular patient. In embodiments where security is a concern, the sharing is only performed between verified organizations (where verification is provided by peer organizations), is auditable by organization administrators and by the patients themselves. Patients also advantageously have the option to add/remove members from their care teams which can also include their relatives, PHRs, and digital devices and applications that generate, monitor, or consume healthcare data (PC2).

The collection of medical records in the standard and ad hoc forms is made possible by the parser 418, the uploader 420, and the parser 422 of the MINE 112. The document parser 418 parses the ad hoc data and whenever possible intelligently categorizes elements of the ad hoc data into structured elements. In some embodiments, natural language processing, neural network, user assisted templates, and other techniques are employed to intelligently categorize these elements. Intelligent categorization is the process of taking a segment of input text and assigning data category and structure based on the data category probabilistically to the segment of text. For example, the text "a1c was reported abnormal"—would be assigned the category "lab result" to the term "a1c" and associate the term abnormal as the result flag to the term "a1c" with some probability. Another example could be "stress test reported no cardiac malfunction" would associate the categories "problem" for the term "stress" and "cardiac malfunction", and the category "procedure" for the term "stress test". It would also associate negation to the term "cardiac malfunction". The document parser 418 then optionally presents the user with its analysis of the potential structured data for review and editing, through the output 117. The document parser 418 creates a standard XML document such as CCD or CCR formats that can be uploaded to the rest of MINE 112 through doc uploader 420. The document parser 418 also can provide users with a graphics user interface (GUI) that will allow them to easily map/identify structured elements in specific types of ad hoc documents to simplify the repeat processing of such documents. For an example, a user could bring up a document on the document parser and highlight the tag PatID: and indicate that the patient ID will follow this tag.

In some embodiments, the document uploader 420 is a computer program that is executed in any security domain. These security domains can be cloud based services, a hospital, a clinic, a personal computer and other suitable forum. The document uploader 420 receives standard XML documents such as CCD or CCR, from the parser 418 or directly from the medical sources 114, and uses this information to verify user information, and securely (usually via SSL) uploads the document to a desired destination within the MINE 112. MINE 112 maintains two main public environments (a product demonstration environment and a production environment) and multiple engineering environments. The type of document uploader employed is optional and a design choice. For example, the particular document uploader 420 employed in the MINE 112 depends upon the connectivity required. Documents can be sent to the document uploader 420 via a variety of methods including but not limited to IHE protocols, web services, shared folders, and drag-n-drop browser interfaces.

In some embodiment, the standard parser 422 is a computer program that is typically executed in a device in the Internet cloud but can, in other embodiments, be executed within a private network environment. The standard parser 422 parses and categorizes standard elements from the XML and creates data objects for specific standard elements. Most uncategorized data is stored as plain text into an ad hoc document object.

Additionally, the document parser 418 and the standard parser 422 advantageously identify and remove duplicate patients as well as duplicate documents. Identification of duplicate patients is done by comparing patient identification, as received by parser 418, from the source 122, to known patients with the MINE 112 and a determination of a threshold number of matches of the patient's received identification. For example, a patient whose social security matches a known patient record within the MINE 112 may be determined to be the same patient or a patient whose last name partially matches another last name and has other matching information, may be declared a duplicate patient. Patients can be matched based on similarities between demographic, clinical, billing, or any other relevant patient records within MINE 112.

The medical knowledge extractor 416 saves medical terms 410 (medical dictionaries, medical ontologies), medical knowledge 412, in digital formats, and medical knowledge gathered from the mapped data objects 434. The medical knowledge extractor 416 creates relationships between different medical concepts found in the medical knowledge. These relationships are stored in a series tables called relevancy matrix 426.

The relevancy matrix 426 are a set of granular tables of medical terms, their synonyms, additional search terms that are of interest and a set of multidimensional relationships that indicate the relevancy of each of the terms (apixions) to other terms (apixion) along various dimensions such as "lab for", "cures", "has reported negative interaction" etc . . . , to medical professionals. The elements in the columns and rows of these tables are called "apixions", also referred to herein as "atomic healthcare related terms". As is appreciated, the set of granular tables grows over time as additional medical terms are identified by the MINE 112.

The relevancy matrix 426 includes tables that are organized at various information levels including but not limited to global information, specialty specific information, standards organization specific information, user specific information, disease or problem specific information, and patient specific information. Advantageously, users selectively and independently adjust their versions of the apixion table by performing a search and then adding or removing elements that they feel are relevant or not relevant to the intent of the search they conducted. The relevancy matrix 426 can process, aggregate, and propagate these user inputs to the other information levels.

The mapper 424 receives the structured and ad hoc medical information and the type (e.g. medicine, allergy, labs, notes . . . ) of information, from the parser 422, and uses the relevancy matrix 426 to generate mapped data objects 434 that include the medical information, the type of medical information and granular terms to which they are related (i.e., the related apixions). Apixions can be used to help identify the same data instances from different sources for reconciliation purposes and to identify similar data instances for comparison purposes. The mapper 424 also consists of a set of flexible rules that can be used to identify exact matches of data instances and "close" matches of data instances. The mapper 424 also records the result of these rules in the mapped data objects 434. Exact matches can be defined as mapped data objects 434 that are identical in the defined fields of interest. Close matches can be defined as mapped data objects 434 that meet some matching threshold on the fields of interest.

The search module 432 is analogous to the search module of the module 232 of FIG. 2 and receives the mapped data objects 434, the relevancy matrix 426 and search input from the user to generate lists of items for each type of medical information. Federated (cached or real-time retrieved data from multiple sources) data is assembled at run time to create a unified view of the patient's clinical history via a set of mappings or rules. Data from multiple sources are either collected in real-time via standards or proprietary query mechanisms or are retrieved from a previously indexed cache of such data. The data from these multiple sources are then combined for a single unified view. What is shown in the unified view depends on and is formed by the data mapper 424 (via de-duplication rules and the data mappings rules) and visualizer 438 which handles the organization rules, rights and privacy rules and the user's role. The search module 432 also ranks the list of items based on their relevancy to various factors such as the user input, a query, relevancy matrix, past user behavior, user role, privacy settings of the patient data, or knowledge gained from history of medical information. These results are passed onto both the visualizer 438 and the API 430.

To summarize, the data from multiple sources is indexed and meta-tagged by the data mapper 424. This data set is then consumed by the visualizer 438. The visualizer presents the same data differently to different end users (or output 117) based on who the user is and what role the user plays in the healthcare spectrum.

In FIG. 4, the API 430, the document uploader 420, and the ad hoc document parser 418 are included in the interface 113 of FIG. 2. The medical terms 410, the medical knowledge 412, the search 432, the visualizer 438, the mapped objects block 434, the mapper 424, the relevancy matrix 426, the medical knowledge extractor 416, and the business intelligence block 436 are a part of the processor 115, and the medical terms 410, the medical knowledge 412, the medical knowledge extractor 416, the visualizer 438, the mapped data objects 434, the mapper 424, the relevancy matrix 426, the standard parser 422, the ad hoc document parser 418, and the template library manager 428 are a part of the processor 116, and the HIE 122, the EMR 120, the HC provider 442, the patient 440, and the health orgs/payers 448 are a part of the outputs 117.

Document and medical data object search ranking is now described. To make medical data objects 434 matching search conditions (Search results 505) even more relevant, MINE makes use of a mathematical concept we call Concept Proximity Model (CPM). The CPM algorithm returns a numerical value indicating the relevancy between a pair of documents or medical data objects 434, or between a medical concept and a medical data object 434. The relevancy value can be expressed in various fashions including but not limited to as an Euclidian distance between two points in a multi-dimensional space, or in angular distance, from −1 to 1, indicating the cosine of the angle separating two vectors with the same dimensions.

To illustrate the use of CPM in relevancy ranking, the following is an example of how a relevancy metric is computed and retuned by CPM that can then be used as part of the search strategy. For any given document CPM calculates a numeric address based on the medical terms (Apixions) in the Relevancy Matrix 426. The numerical address, which can be expressed as a string of numbers or the coordinates of a point in a multi-dimensional space, can be calculated based on various attributes of the medical data in each document (e.g. presence of conditions, symptoms, abnormal labs, etc.) as they relate to Apixions. For instance, let us assume there are only the following three Apixions provided to CPM: medical conditions A, B and C. If a search string inputted by the user is semantically related to conditions A and C, the search criteria can be expressed as a vector, S=[1, 0, 1]. A document that indicates a patient diagnosed with conditions B can be expressed at a vector, D1=[0, 1, 0]. A second document that indicates a patient diagnosed with condition A can be expressed at a vector, D2=[1, 0, 0]. The angular distance, AD, between each document pair can be expressed as a normalized dot product between each vector pairs. In case of the above three vectors, the angular distance between vectors S and D1, would be greater than the angular distance between vectors D1 and D2. This ranking strategy suggests that in case of the above search criteria, document 2 should receive higher ranking and hence be listed closer to the top of the list of search results, than document 1. This ranking is particularly useful in cases where the keyword search indicates that condition A is found in both documents, but is mentioned in document 1 in a way that rules out the condition, as opposed to document 2, that indicates the diagnosis of the condition has been established. In this case, a search strategy using only keywords may not accurately establish the relevance of each document to the search term and may list document 1 above document 2. A simple example would be a document for a healthy patient explicitly listing negatives for each condition (e.g. "no chest pain", "no fever"), which would be incorrectly presented as being more relevant to these conditions than a document in which they are diagnosed positively for a condition.

Reconciliation:

For any given patient or document MINE can calculate a numeric address based on the medical terms (Apixions) in the Relevancy Matrix 426. The numerical address, which can be expressed as a string of numbers or the coordinates of a point in a multi-dimensional space, can be calculated based on various attributes of the medical data (e.g. presence of conditions, symptoms, abnormal labs, etc.) as they relate to Apixions. For instance, let us assume MINE has only the following three Apixions: medical conditions A, B and C. A patient record, R1, indicating that the patient has been diagnosed to have condition A and C can be expressed as a vector, [1, 0, 1]. Another patient record, R2, that indicates a patient diagnosed with conditions B and C can be expressed at a vector, [0, 1, 1]. If we assume that 1) the patient records are comprehensive, 2) all three medical conditions A, B and C to have been accurately diagnosed and 3) the conditions are chronic, then a system comparing the two vectors can conclude with a certain level of certainty that patient records, R1 and R2 do not belong to the same patient, even though the patients may share the same name.

Such a numerical address has a certain level of uniqueness for patients with a fair amount of data points particularly if the patient's record contains many data points that deviate from the norm (healthy) and therefore can be used as a parameter in addition to the patient's ID in order to establish a unique patient identification. The same strategy can potentially be applied to reconciling duplicate documents and data points.

Community-based template review, approval and sharing system is now described. As described above the template lib manager 428 and the visualizer 438 control the display, position, size and behavior of widgets based on pre-defined default and also user-customizable settings. Once an optimal display configuration has been reached, the desired configuration (referred to as a "Template") settings can be submitted to an online community for them to review, test and if desired, rate or even certify the Template. The profiles of the online community and their Template submissions can either be kept private or made public via configurable privacy settings. All users within a community network would have access to the submitted Templates and can test, write reviews or rate the published templates. A decision body or board within a given user network has the ability to certify a Template, making it visible to all users within the community that the Template has received certification. Certification description can have many attributes including date, name of the certification body and other pertinent information.

The capability of "Did You Know?" is now explained. The system searches the history of the patient and displays information that may indicate significant risk for the patient or may have a significant influence on the diagnostic process or treatment plan, based on the patient's "current circumstances". A patient's "current circumstances" includes the patient's current problems, medications, allergies, available measured information (labs, diagnostics, etc) and any active complaints or symptoms they may have. For example, a patient who is complaining of sore throat and fever might have past splenectomy information displayed by the "Did You Know?" feature, since there is a relation between these circumstances and a serious complication due to past splenectomy.

The capability of graphical ongoing display and update is now explained. The system has the ability to display time series information in a variety of graphical formats. Once a piece of information is dragged onto one of these tools, then all data of that type is automatically displayed. As new results are added to the system, they are automatically added to the graphical display. In this case, time series data is any kind o information that can be associated with a date or date range. An example could be a laboratory measurement of Hemoglobin A1 c that is initially dragged to a trend plot tool. All Hemoglobin A1c laboratory results for the patient will be made available to the trend plot for display. Following this, any new Hemoglobin A1 c results would be automatically added to the trend plot display.

Further details of the functions of the processor 116 of FIG. 2 are now provided.

Figure 5:
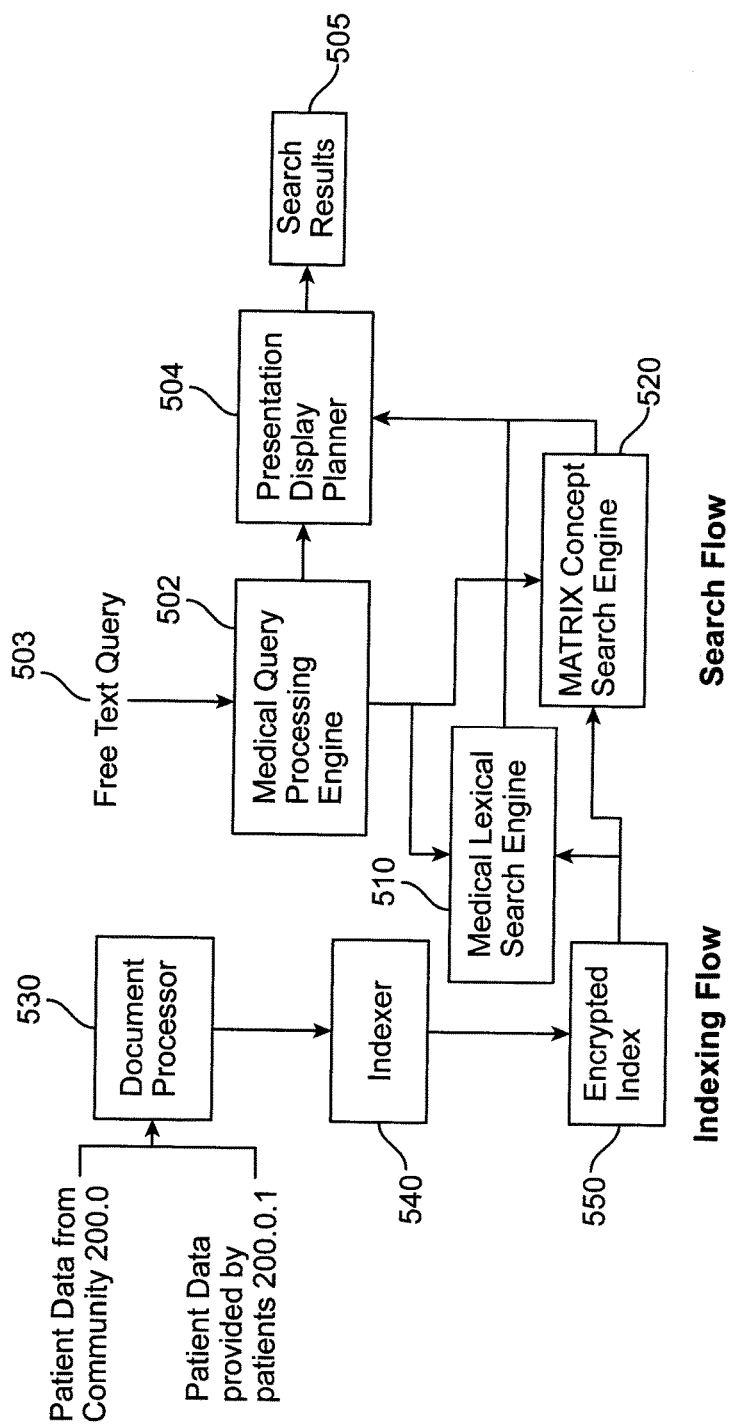
FIG. 5 shows a block diagram of the indexing, querying, and searching functions of the MINE 112, in accordance with a method of the invention.

Indexing and Meta Tagging:

FIG. 5 shows a block diagram of the indexing, querying, and searching functions of the MINE 112, in accordance with a method of the invention. An indexer 540 is shown to receive documents from the document processor 530 and to provide indexed documents to the encrypted index module 550, to be encrypted. The medical query processing engine 502 receives a free text query 503 and processes the same and provides the processed query to the medical lexical search engine 510 and to the matrix concept search engine 520. The engines 510 and 520 also receive the encrypted document from the module 550 and provide a medical search engine output and a matrix search engine output, respectively, to the presentation display planner 504. The planner 504 ultimately provides search results 505 as its output. The engine 502 also provides output to the planner 504.

The document processor 530, indexer 540, and module 550 are generally located within the processor 116, in one embodiment of the invention. The engines 502, 510, and 520, and the planner 504 are located within the processor 115, in one embodiment of the invention.

The document processor 530 receives community patient data 200.0 and patient-provided patient data 200.0.1 for processing. The data 200.0 is provided from sources other than the patient whereas the data 200.0.1 is provided by the patient.

The engine 502 converts free form natural language queries, free text query 503, into calls to the engines 510 and 520. The engine 510, in a predetermined collection of medical data objects (such as text documents, structured or ad hoc), finds all objects having the keyword term match (perfect or loose) anywhere in the content of the medical data object and filters them using other keywords. The engine 520, for a predetermined collection of medical terms, finds a list of medically related terms, identified through a knowledge base comprising medical terms, semantic relations, and strength of the relations. The collection of medical terms is dynamically changing according to user-input and otherwise, as the system 100 gains medical knowledge. The planner 504 converts the output of the engines 510 and 520 into a unified display plan for viewing by a user and this becomes the search results 505—medical data objects that can be matched to either keyword or concepts.

Two data flows are shown in FIG. 5. Indexing flow follows the flow of data from the 200.0 and/or 200.0.1 to the processor 530, the indexer 540, and the module 550, to the engines 510 and 520. Search flow follows the flow of data from receipt of the query 503 to the engine 502 to the engines 510 and 520 to the planner 504 to generate the search results 505.

In the search flow, the engines 502, 510, and 520 are used to process documents and convert them into formats that make them easy to quickly search and retrieve from a large collection of documents. The indexing flow allows for reliable and automatic replication of documents across multiple physical machines. Indexing also supports large throughput (large number of documents getting indexed per minute) because it can split the work load over a large number of machines, such as multiple processors. The indexer 540 converts the incoming healthcare data into a form that makes the querying faster. The indexer 540 also stores the contents of the data in a completely encrypted format so that in case of data theft, the protected health information (PHI) is not revealed.

The module 550 stores patient data, which it receives from the indexer 540, in the form of an indexed document, in an encrypted format that is also easily searchable and generates encrypted indices. This encryption protects patient data from data theft. In alternative embodiments, the encrypted indices, generated by the module 550, may be stored in multiple processors and queried independently—thus they are fault tolerant and protect PHI.

The search engine, of the various embodiments of the invention, is built around the concept of Zero-Click Relevance—or the ability to get all the relevant information a provider requires by entering a single query. That is, all relevant information, required by a medical provider, may be retrieved upon receipt of a single query.

As described previously relative to FIG. 5, the search engine consists of two distinct components—namely the indexing flow and the search flow. The indexing flow consumes patient data from the community (in multiple formats including CDA templates, CCR, CCD, PDF, images, etc.) as well as data provided by the patients themselves. Patient-provided data can come in the form of patient uploaded material such as status updates or images, videos and documents or can be from health monitoring devices connected to the internet. The indexing flow processes each of the documents received by the system and converts them into structures that make the searching of this data efficient (Indexer 200.2). These structures are stored in a completely encrypted fashion to protect patient information.

The search flow takes as input a free text query (i.e., a query without any restrictions on the structure)—and converts the free text query into commands to the Medical Lexical Search Engine and the MATRIX (Medical Application Terminology Relationship IndeX) Concept Search Engine using a sophisticated query processing engine optimized to work with medical queries. The results of the search engine are sent to the presentation display planner 504)—which decides the most relevant presentation given the users role and privileges and their organizations roles and privileges (e.g. provider, administrator, quality manager, and the patient) and the search query.

Figure 6:
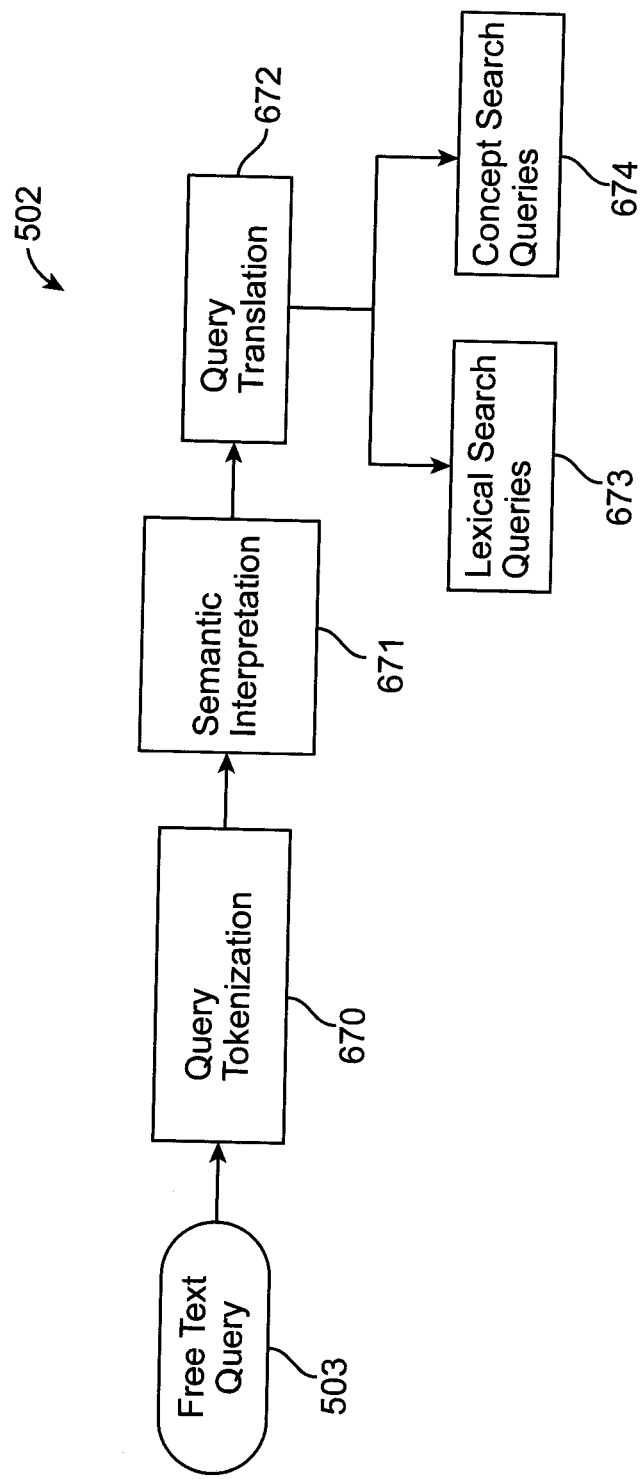
FIG. 6 shows a block diagram of the query module, in accordance with an apparatus and/method of the invention.

Query:

FIG. 6 shows a block diagram of the query module, in accordance with an apparatus and method of the invention. The query module 502, also referred to herein as "medical query processing engine", is a part of the module 232 of FIG. 2 and is shown to have the free text query 503 received by the query tokenization module 670, which is shown to provide tokenized query to the semantic interpretation block 671, which, in turn, provides interpreted semantic results to the query translation block 672. The block 672 provides query translation to the lexical search queries block 673 and the concept search queries block 674. The engine 502 converts free form natural language queries, or the free text query 503, into input that can be used by the engines 510 and 520 by first tokenizing the query 503, performed by the block 670, using a large dictionary of medical terms to identify all possible interpretations of the terms in the query. An interpretation for a query consists of all the medical terms that were found in the query along with their medical types. Thus, tokenizing a query, in some embodiments, uses a dictionary of medical terms to identify all possible interpretations of the terms in the query. It also consists of any relation that can be recognized between the medical terms in the query based on function words such as "with" and "of".

Each interpretation is scored based on the surrounding context, for example, other words, medical terms and relations present in the query, or the knowledge provided by the application to the query processor such as the history of previous queries and user responses. After scoring all interpretations that are generated, the interpretation with the highest score is chosen as the most likely interpretation of the query. The most likely interpretation of the query is translated into a lexical search query 673 and a concept search query 674 and sent to the lexical search engine 510 and the concept search engine 520.

The most likely interpretation is then transformed into calls to the engines 673 and 674 for lexical and concept search, respectively. Once the results are returned from the searches the query processing engine annotates the returned results with information about the query so that it can send it to the display planner to create an appropriate display plan.

Figure 7:
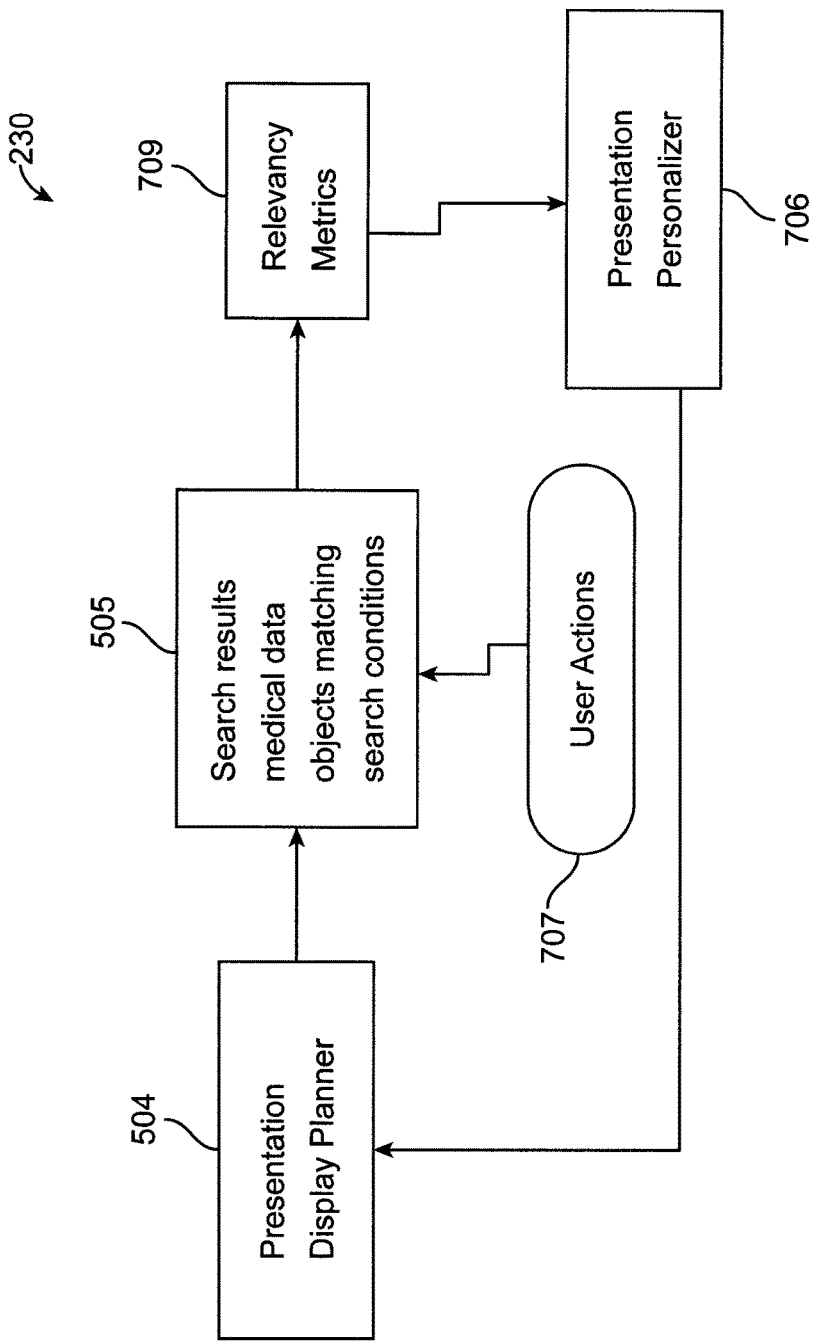
FIG. 7 shows a block diagram of the relevant blocks/functions of the presentation module of the module 230 of FIG. 2.

Presentation:

FIG. 7 shows a block diagram of the relevant blocks/functions of the presentation module of the module 230 of FIG. 2. A presentation display planner 504 is shown to receive input from a presentation personalizer 706 and to provide search results 505 that are in the form of medical data objects matching search conditions. The search results 505 receives user actions 707 and serves as input to the relevancy metrics block 709, which is shown to provide input to the presentation personalizer 706.

The planner 504 receives, as input the annotated results for a query, from the personalizer 706, and converts them into an ordered (ranked) list of results to be presented to a user. The ranking component includes exhaustive medical knowledge available in MATRIX to decide the relevance of data objects. Each result can be different in its presentation. The planner 504 also records user actions 707 on the output of the search results such as user clicks and dwell times. This information is logged internally for computing relevancy metrics and to provide personalization. For example, a result containing laboratory results can be displayed as a trend line over time whereas results containing problems can be displayed with special markers indicating the onset of the problems, related medications and procedures for the problem. A problem or condition that has been cured can be displayed differently from a present problem to indicate that the problem is no longer active. Apart from creating display plans for each result, determining its styling, content, and presentation (for example, graph vs. highlighted text) the display planner also determines the global order of results. For certain types of queries (for example, queries about analytes and lab tests) certain types of results might be prioritized over others.

The planner 504 uses logged relevancy metrics along with user data to personalize the presentation for the user and the query. On every query and user this data is captured and stored. A periodically running background task, the personalizer 706, analyzes the relevancy metrics captured for each user and query and converts them internally to a personalization model which is applied when presenting the search results to the user at query time. This process creates a feedback loop increasing the relevancy of results returned for each user.

Search:

Medical Lexical search, as performed by the engine 510, extends a traditional text search engine by implementing a medical term analyzer, which makes the search engine aware of the specifics of medical terminology. For example, search for "heart attack" should find only occurrences of the whole term and disregard occurrences of "heart" and "attack" as separate words. Another example: search for "Alpha-1-Fetoprotein" should match "-1-Fetoprotein" too.

Search can be performed using each of three following basic search algorithms:

Perfect match (default)—finds all the occurrences of a given set of search terms appearing in the searched text in original order. The searched text and search words may be stemmed, stripped of stop-words and converted to the lower case before matching.

Loose match—Finds all occurrences of a given set of search terms in a collection of documents appearing in any order in the search text within N positions of each other. Here, N is a matrix of numeric values, which give the maximum and the minimum amount of characters that may appear between any pair of search terms.

String match—The third search algorithm, used by the medical lexical search engine 510 matches strings of characters as opposite to whole words. Since this search can find matches to part of a word, it is useful for the auto-complete function and the search suggestion box in the user interface.

Figure 8:
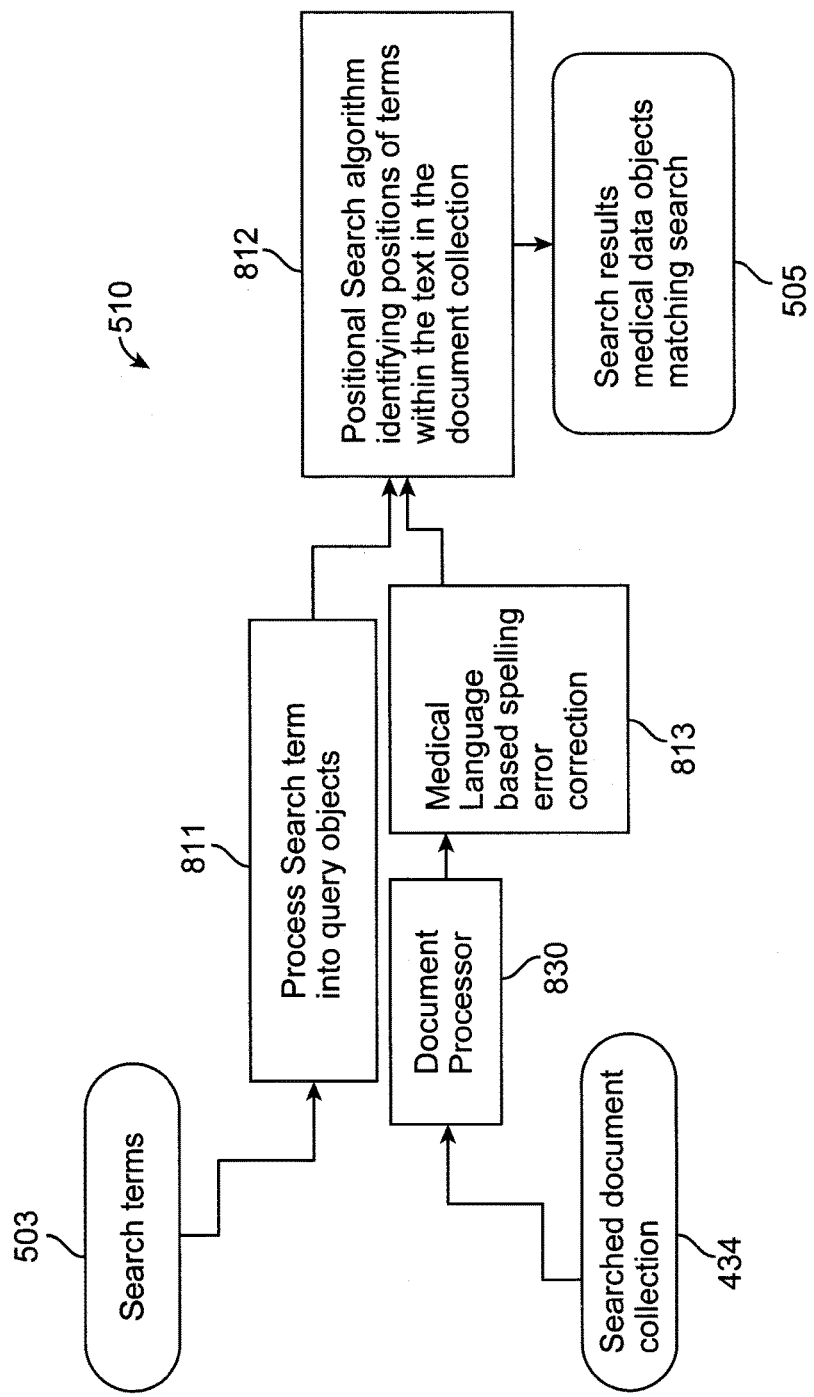
FIG. 8 shows further details of the medical lexical search engine 510, in accordance with an embodiment and method of the invention.

FIG. 8 shows further details of the engine 510, in accordance with an embodiment and method of the invention. The search terms 503 and the search document collection 434 are received, the former by the process search term into query objects block 811, and the latter by the document processor 830. The processor 830 processes the searched document received from the collection 434 and sends the same to the medical language based spelling error correction 813, which corrects misspellings and sends the corrected text to the Positional Search algorithm 812 for identification of positions of terms within the text in the document collection, with the final search results 505 of medical data objects matching the search. The search terms 503 is received by the block 811, which processes the search term into a query object.

Figure 9:
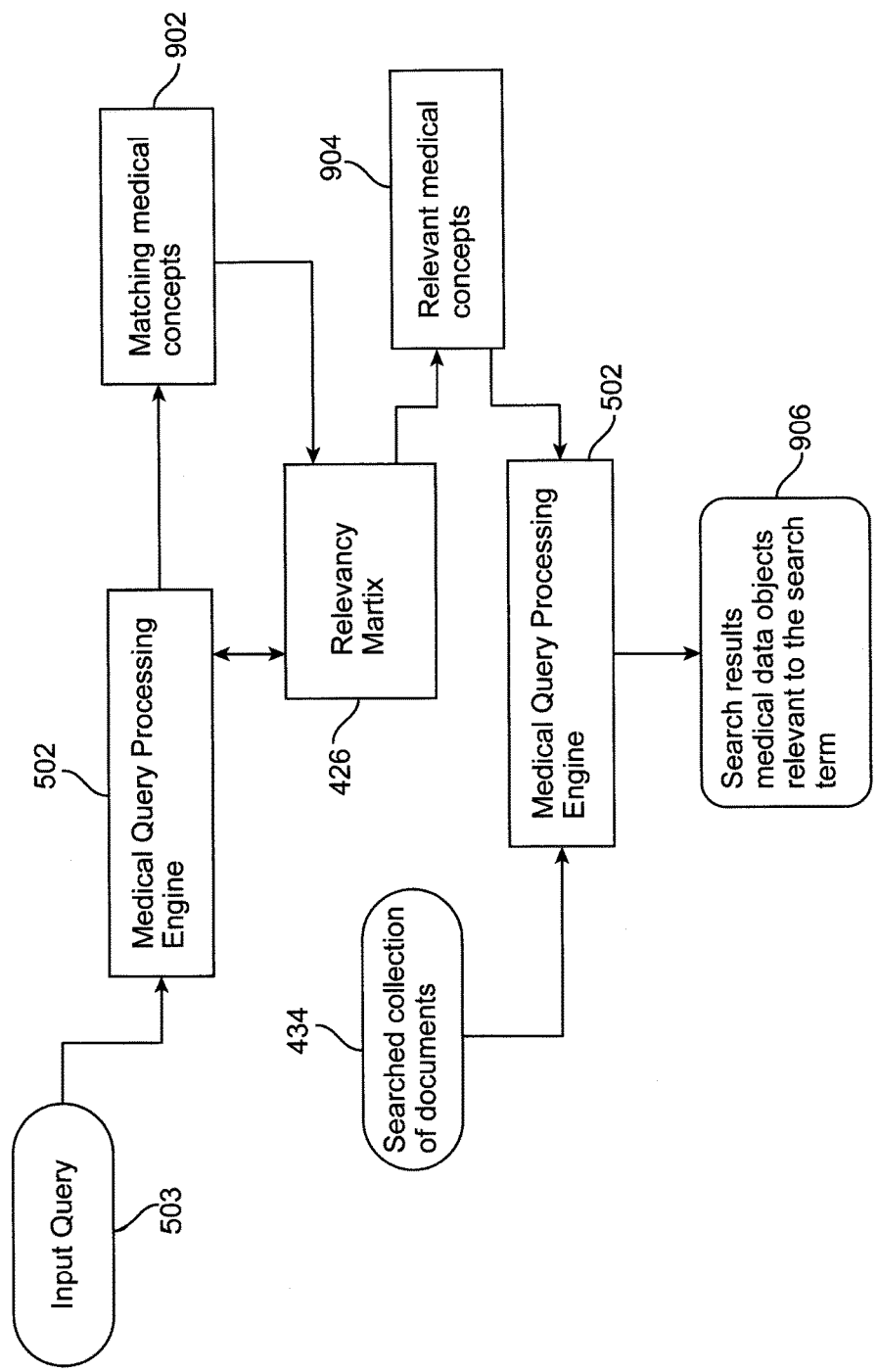
FIG. 9 shows further details of the MATRIX concept search engine 520 of FIG. 5, in accordance with an embodiment of the invention.

FIG. 9 shows further details of the engine 520 of FIG. 5, in accordance with an embodiment of the invention. The input query 503 is received by the medical query processing engine 502 which processes the received query using the relevancy matrix 426 and outputs from the processed query a set of matching medical concepts block 902. The relevancy matrix 426 uses the matching medical concepts block 902 and filters it to generate only the relevant medical concepts (block 904). The relevant medical concepts block 904 obtained as the output received from the matrix 426 is fed back to the medical query processing engine 502. The engine 502 further receives searched collection of documents 434, which in combination with the relevant medical concepts block 904, is used to generate search results 906. The search results 906 includes medical data objects relevant to the search term, as previously discussed.

The engine 502 is knowledge-based and includes a table of medical terms, concepts, relational links between concepts and numeric values (relevancy scores) providing a quantitative measure of the strength of the relational links. This collection of numeric values is referred to herein as the relevancy matrix 426. The normalized relevancy score has a range between 0 and 1, with 0 being completely unrelated (orthogonal) and 1 been highly related (e.g. synonymous). It is noted that in other embodiments, the opposite or a different range may be employed, for example, 1 may be used to reference unrelated and 0 may denote highly related. The relevancy scores are obtained through a collection of machine-learning algorithms that operate over collections of data obtained by a variety of sources, including, but not limited to, data generated by experts and medical practitioners including clinical data stored within the system, data obtained from usage statistics and data obtained by converting publicly available medical texts into knowledge usable within the matrix.

In order to identify all the concepts relevant to the search term, the knowledge base is queried with the search term to find all the concepts that are related to the search term. When all the matching concepts are found, the relevant items can be selected by filtering the list of returned concepts based on their relevancy score. The threshold for filtering is a relevancy search parameter that determines the stringency of the algorithm, from selecting only synonyms to finding all remotely related concepts.

The identified list of relevant medical concepts is passed as an input to the medical query processing engine which is then able to generate relevant lexical queries for the lexical search engine 520 to return the search results 906.

An additional level of complexity in identifying relations between medical terms is created by negative semantic constructs. For example, occurrence of the words "diabetes ruled out" in the context of a medical document needs to be interpreted by the relevancy engine as a negative relevancy value for diabetes. From the semantic algorithm perspective, two main problems associated with negations are detection and interpretation. Negation detection algorithm relies on the collection of negative semantic constructs found in the medical texts and falling into several categories, from simple negation, like "no fever", to more complex patterns like "no sufficient evidence of infection". The negation detection algorithm uses a machine learning model to learn structural patterns in sentences to identify if the phrases in the sentence are negated or not.

Interpretation of negative relevance values depends on the specific use case. When application requires only detection of relations between concepts with no discrimination for their type, negative relevancy values can be used as absolute values. However, building decision support elements requires understanding of the semantic interactions between medical data objects, so interpretation of negative relevancy values becomes critical.

FIGS. 10-19 show various screen shots of search results, in accordance with exemplary embodiments of the invention.

FIG. 10 shows a screen shot of an exemplary search result 906. Patient Joan Sample's information and lab results are presented showing ranges of her various test results with these results characterized by the relevancy matrix, in accordance with the discussion above. For example, calcium is noted having a relevancy value of 0 while glucose is noted to have a relevancy value of 1.0.

FIG. 11 shows a screen shot of an exemplary output from Apixio Search 432 as presented by the visualizer 438.

Figures 12, 13, 14:
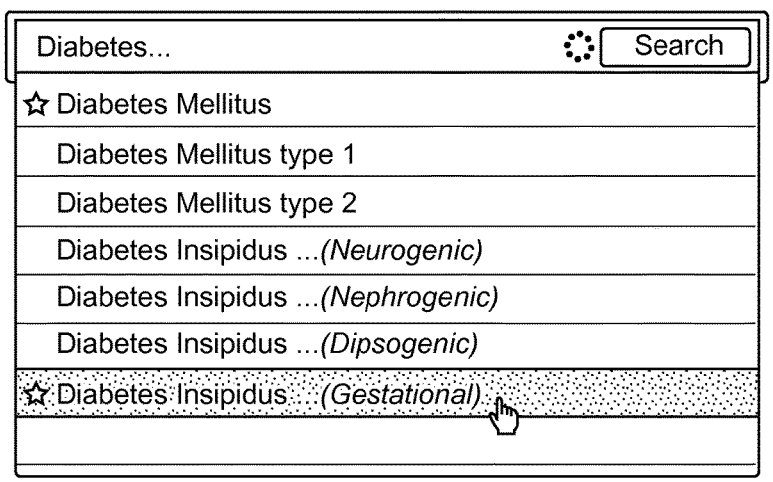

FIG. 12 shows a screen shot of an exemplary page of a display to the user with default status showing. At the start, the page is empty of most/all widgets, featuring a welcome widget. Visible items include Input bar and associated tabs (Patients, Favorites, History), a Settings link, and a Sign Out button. Upon the user typing in the input, a drop-down of potential patient names, conditions, or related searches appears. Patient matches listed in the drop-down include matching on first-name, last-name, and nicknames/psuedonames (ie. "John Doe Feb 5") if necessary. (birthdate, ID?) Down-key begins navigating the drop-down list. Up and Down keys can step through the list, where the current item is highlighted visually. Similarly, mouse-over on the list highlights drop down choices. As shown in FIG. 13, a click (touch) selects the item, thus populating the input-field.

If the user begins or resumes typing characters or presses backspace, the stepping process stops and the functional process resumes to compiling and narrowing the list of choices. If the list exceeds 10 items (desktop) and 6 items on mobile devices, the list accommodates pagination elements. The bottom strip of the panel should display a "next . . . " feature. When the "next . . . " feature is used/accessed, the top-most segment displays (changes to) a "prev . . . " feature. The Next and Prev (displayed at the bottom and top respectively) should not be accessible by up and down arrow. However a Right or Left arrow key-press should activate/ flash their appearance and paginate the list forward (right-arrow) and backward (left-arrow). On touch devices, a press of either Next or Prev, paginates forward and backward along the list. As with known search standards (Google, Yahoo, etc), each keystroke narrows the field of possible pre-selected choices. If no matches result, the list will disappear.

List choices that are already in a corresponding panel (such as an admitted patient, or prior condition patient has been seen for) render prefixed with a star. If the Health Care Provider (HCP) enters a query item with no matching records, a search results widget or pane in general the page should list all related possibilities in a list format.

An exemplary item selection is as follows:
Tab key or Enter key press selects the highlighted item and locks the parameter as an object. A mouse-click on a list item selects the highlighted item. A click or touch selects the list item.
Once an input item is selected from a drop-down, the corresponding input overrides (or completes) to match the official listing, and changes visually becoming blue, appended by a + symbol to indicate the item is an object.
The patient-search object can then be operated on.
1. Search/Input Objects
Once search or input item is selected, it transforms visually into an object. As objects, input field items can be operated on.
Dragging the Patient-object to the Patients tab adds the patient to the Patients tab.
Dragging the Complaints-object to the Favorites tab adds the item to the favorites list.
Dragging objects to an operational widget may act upon that object (as a phrase or parameter that defines the widget.

General Search/Input box behavior is now discussed, as follows with an exemplary screen shot shown in FIG. 14:
If patient has not been identified, then the patient matches or organization/cohort/panel matches (for population search) are prioritized in the dropdown list.
Once patient name or population group is locked/identified, the drop-down list features medical-terms and NOT patients or population groups.
Backspace over any single item, mid-phrase or upon the plus-sign or other delimeter, will unlock that Object (rendering in gray/default) and redefine the items on the page.
Backspace deletes within the terms and phrase, character by character.
Escape will bring back the last object
Double clicking on a word selects the entire phrase (multiple words comprising the term).
Unrecognized words and terms become a "Keyword Object" and are featured in orange after being operated on by a search.

Figure 15:
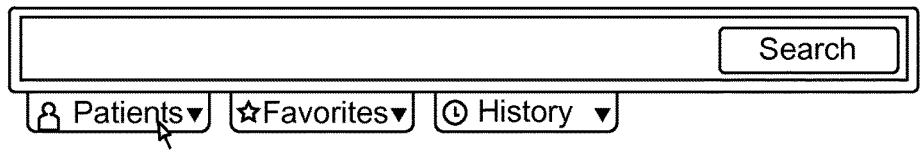
Figure 16:
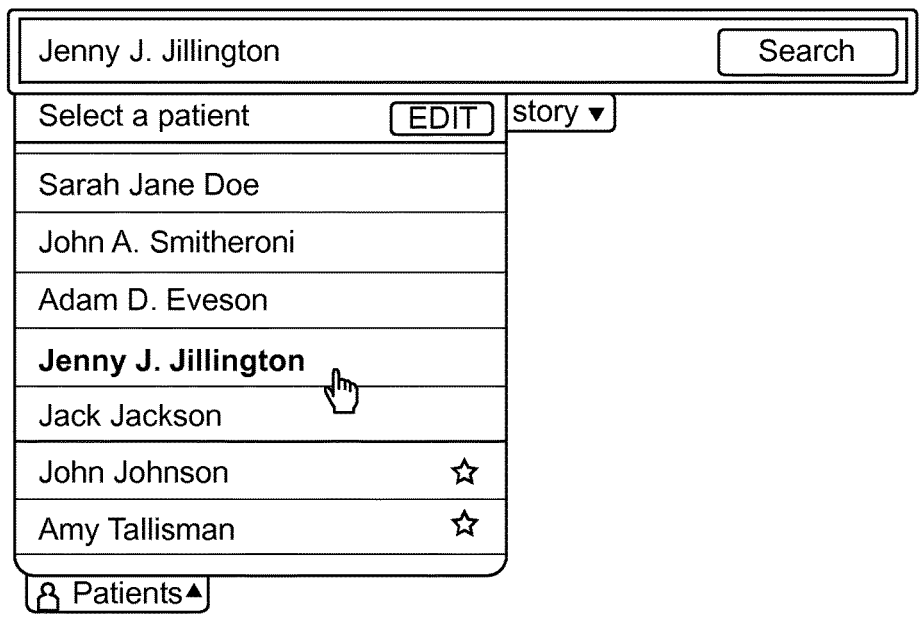

Tabs and panels, are shown in an exemplary screen shot, in FIG. 15, and are as follows. Clicking on a tab opens the corresponding panel (using a JQuery animation) and changes focus to the list (auto-selecting the first one), as shown in FIG. 16. In this mode, typing keystrokes jumps to closest matching list-item. 'Up' and 'Down' arrow steps through the list. 'Tab' or 'Enter' selects the highlighted favorite item, thus populating the search/input box. 'Esc' (escape) closes the panel and returns focus to the existing search/input. After a panel opens, its tab features a reversed triangle icon indicating it will close. Click/touch of the tab or Close icon, or press of the Esc key will close the panel and return focus to the Search/Input. Clicking outside the panel will also close the panel. Selection of a panel list's item closes the panel and returns focus to the Search/Input. The panels features an 'Edit' button for a list management capability, as shown in FIG. 16.

Figure 17:
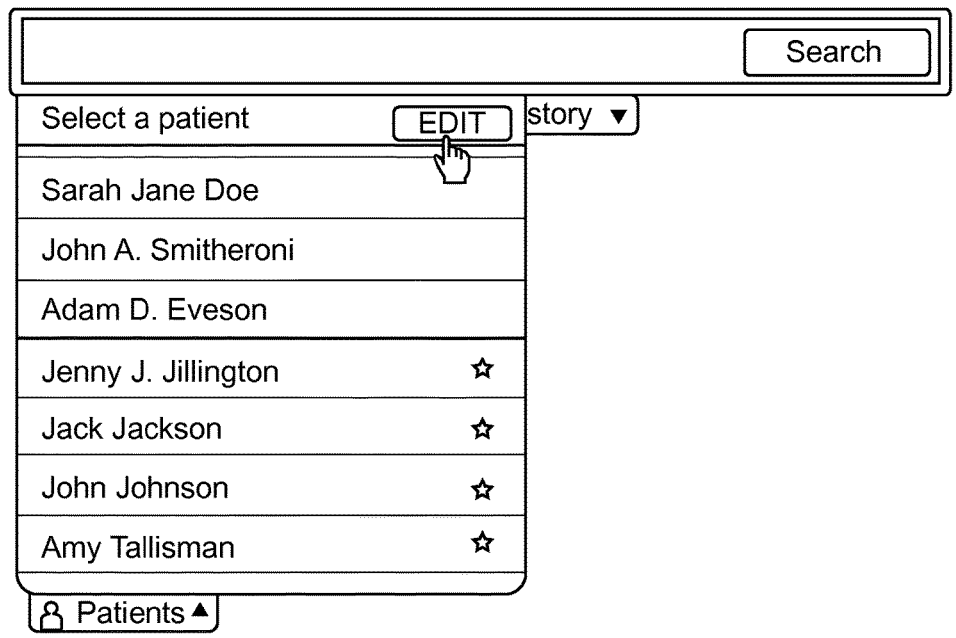
Figure 18:
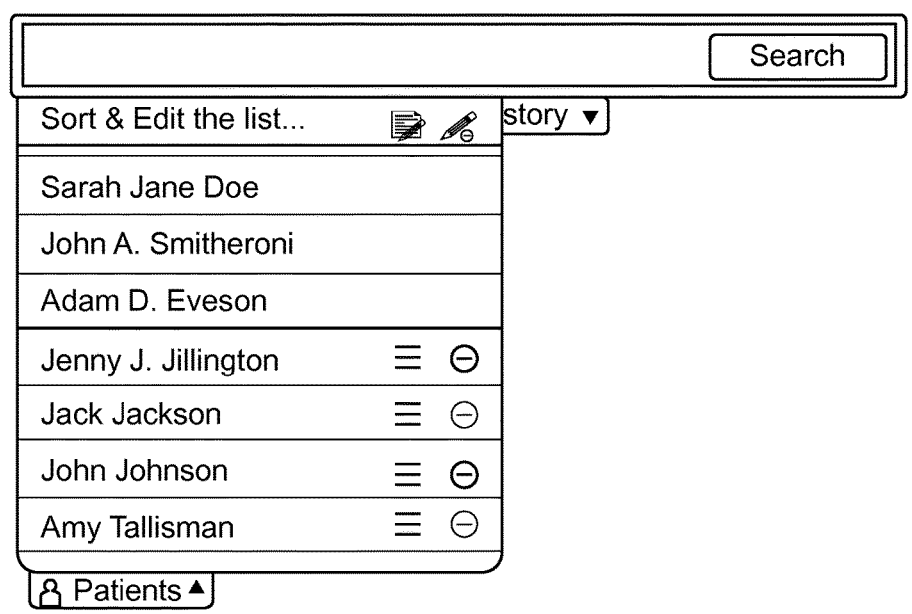

Panel edit mode is shown in FIG. 17 and operates as follows. Clicking the 'Edit' button transforms the panel to feature 'move' icons and 'delete' icons after each item in the list, as shown in FIG. 18. Delete icons are grayed-out by default.

Click on the 'Delete' icons toggle the icon between gray and red modes. Dragging (mouse or touch) of the list item repositions the item in the list. A 'Delete' activator icon and an 'Edit' icon replace the 'Edit' button. Click of the 'Delete Activator' icon deletes all items toggled "on" in the list, and the list stays open. Click of the 'Edit' icon ends the list management mode (and returns to view of normal open panel).

The 'Patients Tab (Panel)' is as follows. The panel contains a list of patients the user has dragged to the Patients tab, ranked in the order they have been added (last item goes at the end). This list functions as a short-list of patients the HCP is monitoring closely. Features scheduled-patients in chronological order (listing all the days patients). Patients already seen should be subdued (visually less apparent). Upcoming patients should be visually neutral. Admitted patients (i.e. checked-in by clinical staff), should stand out visually prominent (be highlighted). Selection of an item from the Patients panel replaces all items in the Search/Input box and locks in the Patient parameter.

The favorites tab (panel) is as follows. Features a list of chief-complaints and disorder items is selected by the HCP for quick access. If the Patient Parameter has been locked in, features a list of chief-complaints the patient has been seen for.

The History Tab (List) features a list of complaints the patient has previously been seen for, listed chronologically with the most recent on the top. The settings feature is used by clicking the Settings link to activate a lightbox popup with the following parameters for the HCP to set their preferences. Table 1 below is an exemplary table of the setting link, activated.

TABLE 1

| Setting | Function | Options |
| --- | --- | --- |
| Patient name order | | |
| Auto-signout | Sets the time parameter | Off, 1-minute, 3-minutes, 5-minutes, RFID departure |
| Future settings | | |
| Language | Sets the language | TBD |

Figure 19:
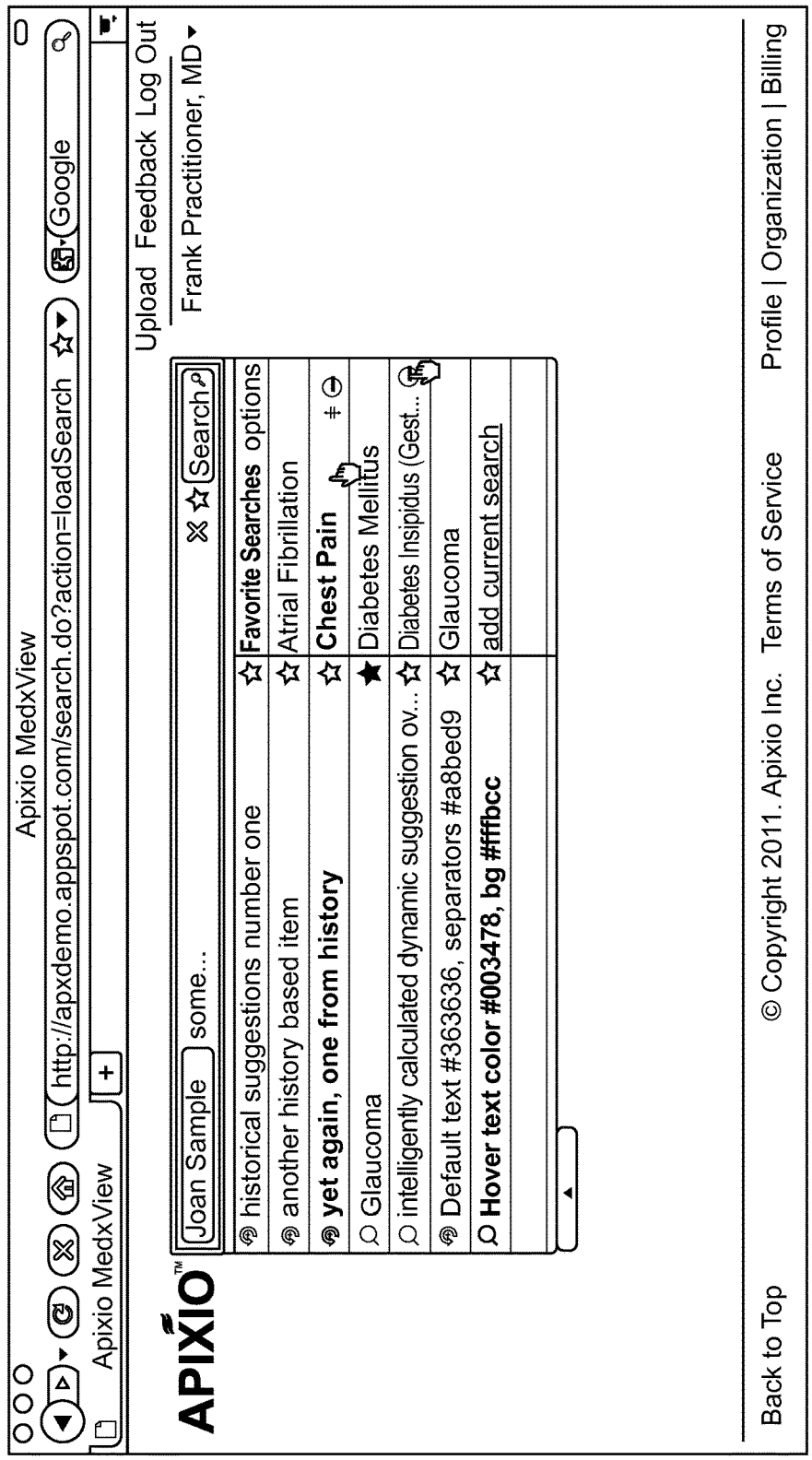

An alternate view is to provide suggested searches based on multiple parameters such as the user's specialty, their historical searches, the patient's data and any other parameters that can be used to predict the user's desired search intent. This dropdown could also show other items such as favorite searches. This search is modality is shown in FIG. 19.

Visualizer:
The search 432 module takes the mapped data objects 434, the relevancy matrix 426 and search input from the user and creates lists of items for each type of medical information. The search 432 also ranks the list of items based on their relevancy to the user input. These results are passed onto both the visualizer 438 and the API 430.

The visualizer 438 takes the search context input from the user in a natural language text box and provides widgets that react to the search context to provide specific mapped data objects 434 that are relevant to the context. In addition the widget content, the layout of the widgets themselves can be context driven. The layouts can be standardized by the template lib manager 428. Examples of context include but are not limited to patient, problems, diseases, specialty, laterality, and demographics. There are multiple types of widgets, those with access to protected health information (PHI) and those without access to protected health information. Example of a PHI Widget would be a widgets that brings up meds, labs, allergies, problems, diagnostic reports, office notes and so on. The PHI Router 2006 is responsible for routing the authorized data to each of the widgets. These types of widgets can receive the mapped data objects 434 in addition to context information, they can then combine the received information with other local or web based information to produce unique context relevant display for the users. Example of non-PHI Widgets include widgets that display sponsorship, encyclopedia, or ad information in response to the given non-PHI context such as problems, or diseases.

The visualizer 438 also makes it easy bring up frequently requested contexts (e.g. favorite patients, diseases or problems). Further details of the visualizer 438 GUI are found in the UX design document. The visualizer 438 also takes the search result by type and performs additional type based processing such as data reconciliation between multiple items of the same type from different sources. The displayed text and coding system of data presented by the visualizer 438 can be customized based on viewing user's preferences. The data reconciliation can be automated as well as user assisted. Depending upon the type of data and the type of matching, the reconciliation can be performed at import and persisted in the database or can be performed for display purposes only by the visualizer 438. Mapped data objects 434 are reconciled by the visualizer 438 in multiple ways based on whether they are exact matches of the same data instance, a potentially "close" match of a given data instance, or are identified as a the same type of data for comparison purposes. Rules for data matching and discrepancy flagging can be based on organizational or locally defined preferences, rules and/or mappings. Exact matches can be combined on display without flagging. Depending upon the data type close matches are either combined with a flag indicating a reconciliation occurred or are flagged (or marked) to indicate a potential reconciliation could occur.

The visualizer 438 can also take input from the user (healthcare provider 442) as to the level of relevancy of the information that they are interested in. The visualizer's 438 layout can also be customized by the user and by standards organizations who can use the template library manger 428 to manage and publish context specific layouts. The template library manager 428 can manage layouts at the individual, group, specialty, and standards organization level.

Figure 20:
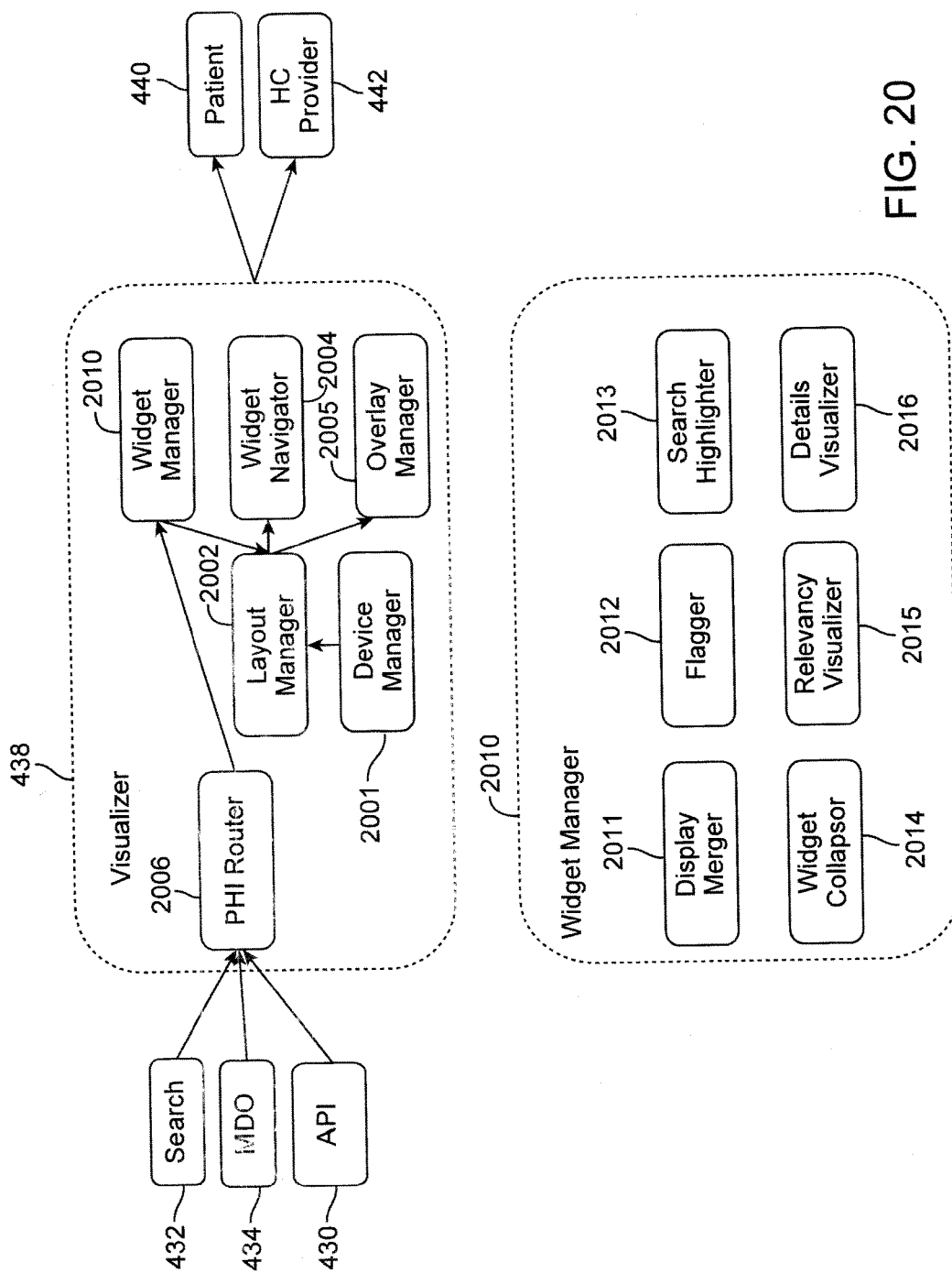
FIG. 20 shows further details of the visualizer 438, in accordance with an embodiment of the invention.

FIG. 20 shows further details of the visualizer 438, in accordance with an embodiment of the invention. The term "widget", as used herein, refers to a developer-created entity that populates the module spaces in the page, including all code, and its integrating components. A developer is a third party or a user of the MINE 112. The arrows linking the blocks of FIG. 20 show the major data flows, other connections between the modules and data flow in the reverse directions are anticipated. The functions of the blocks of FIG. 20 are as follows:

1. The Device Manager 2001 manages the major device specific layout and functionality differences.
2. The Layout Manager 2002 manages the location, size, and repositioning of the widgets.
3. The Widget Manager 2010 manages the content of each of the widgets. Key functionality includes:
    3.1. Display Merger 2011 functionality combines multi-sourced items for a simple view of the data, it can take into account the among other things type of data, the sources, and who is viewing the data.
    3.2. Flagger 2012 provides visual feedback on the state of merged items
        3.2.1. No pill is displayed if multi-sourced items are considered the same by organizational specific rules.
        3.2.2. Gray pill is displayed if multi-sourced items are considered similar by the organizational specific rules.
        3.2.3. Orange pill is displayed if the multi-sourced items are merged manually.
        3.2.4. Other colors could be used for further annotation of merged items.
    3.3. Search highlighter 2013 highlights items that are relevant to the search performed
    3.4. Widget collapse manager 2014 collapses widgets that are do not return relevant information
    3.5. Relevancy visualizer 2015 provides mechanisms to gather specialty/user specific feedback on the relevancy of items by display lower relevancy items in a compact form such as a comma separated list and allowing the user increase its display relevancy by clicking on it
    3.6. Details visualizer 2016 provides the ability to see all the details of an item by clicking on it, hovering over it, or other user gestures or actions
4. Widget Navigation 2004 allows users to rapidly get to the widget of interest and may affect the search bar/query content
5. Overlay Manager 2005 displays large drill down data (eg. office notes or images) in the main window as an overlay. Overlays can contain one object at a time or can contain multiple objects for comparison purposes.
6. PHI Router 2006 routes data from the mapped data objects 434 to the appropriate widgets based on the type of widget and the type of information it needs to display. The PHI router can discriminate between may types of indexed, mapped, and consolidated data and takes into account the user's role and organization and the security policies governing each discrete medical data item and its meta-tags.

The API 430 exposes the search bar and search results to third party programs as well as allows third parties to publish their data in widgets presented by the visualizer 438. As an example, the search bar and search results can be embedded securely into third party programs using either a REST or SOAP APIs. Examples of security mechanisms include encryption, authentication credentials, context, and tokens. Third party developers can take context information provided by the search API (for example by a secure SOAP API) and combine it with their own data to produce customized widgets and data in the visualizer 438.

FIG. 21 shows a computer display or screen shot of the consolidated (reconciled and de-duplicated data), in accordance with an exemplary output processed by the mapper 424 and presented by the visualizer 438. The flag, for example, a pill shaped icon with a number in it, indicates the number of records that were merged. Clicking on the flag allows the user to see the merged records, change the one that is displayed, the master record, and/or unmerge the records. Mapped data objects 434 that are merged or unmerged by users can be propagated to all users within an organization, or on the Care Team of the patient, thereby building an improved Wiki-styleview of the patient. This propagation of user edits can also be performed across organizations.

Although the invention has been described in terms of specific embodiments, it is anticipated that alterations and modifications thereof will no doubt become apparent to those skilled in the art. It is therefore intended that the following claims be interpreted as covering all such alterations and modification as fall within the true spirit and scope of the invention.

The invention claimed is:

1. In a medical information navigation engine (MINE), a computerized method of transacting health information comprising:
receiving a health information request (HIR) from a user, wherein the HIR is a text query;
retrieving health information in response to the HIR using a medical information navigation engine (MINE);
meta tagging the health information by associating the health information's content with medical concepts using a relevancy matrix with rows and columns, wherein the relevancy matrix provides probabilistic associations between medical concepts, lab procedures, physiological measurements, medications and allergies, and wherein the elements in the rows and columns of the relevancy matrix are apixions;
searching the health information and the meta tags for the apixions matching terms in the text query to identify relevant health information; and
providing the relevant health information to the user based upon the user's role, wherein different user roles receive different relevant health information.

2. A method of transacting, as recited in claim 1 further including determining the most relevant access to be provided to specific relevant data based on a search query, a patient, and the user's specific function/role and security privileges.

3. A method of transacting, as recited in claim 2, further including exposing search results to third party programs and allowing third party programs to publish their data.

4. A method of transacting, as recited in claim 3, further including securely embedding the search results into third party programs using application programming interfaces (APIs).

5. A method of transacting, as recited in claim 1, further comprising indexing the health medical information.

6. A method of transacting, as recited in claim 5, wherein indexing includes receiving processed documents and converting them into formats that allows for quick searching across a large collection of documents.

7. A method of transacting, as recited in claim 5, further including assembling of cached or real-time retrieved data from multiple sources for a unified view via a set of mappings or rules.

8. A method of transacting, as recited in claim 7, wherein the set of mappings or rules include flag indicators.

9. A method of transacting, as recited in claim 5, further including meta-tagging information extracted from images to enhance recall of search queries.

10. A method of transacting, as recited in claim 1, further including at least one of Wiki-based quality checking of relevant health information and Wiki-based commenting of relevant health information.

11. A method of transacting, as recited in claim 1, further including converting the text query into search commands.

12. A method of transacting, as recited in claim 1, further including query language to provide systematic access to various parts of a patient record.

13. A method of transacting, as recited in claim 1, further including sharing certain patient data between organizations/systems based on a "need to know", semantics, mappings, user roles, or user preferences.

14. A method of transacting, as recited in claim 1, further including inviting members of a care team to join thereby allowing distributed user-organized care teams.

15. A method of transacting, as recited in claim 1, further comprising searching and routing uploaded information including status posts, records, or images.

16. A method of transacting, as recited in claim 1, further including ranking of results based on the query and knowledge.

17. A method of transacting, as recited in claim 1, further including identifying a plurality of possible interpretations of the terms in the query.

18. A method of transacting, as recited in claim 1, further including performing concept search on the health information.

19. A method of transacting, as recited in claim 1, further including retrieving relevant information required by a medical provider upon receipt of a single query.

20. A method of transacting, as recited in claim 1, further including processing the medical information or user-related information to suggest relevant queries.

21. A method of transacting, as recited in claim 1, further including tagging information to extract discrete medical information from a text source.

22. A method of transacting, as recited in claim 1, further including performing business intelligence queries including searching across populations.

23. The method of claim 1 further comprising using the apixions to identify different data instances for reconciliation purposes or to identify similar data instances for comparison purposes.

24. The method of claim 1 further comprising consolidating the relevant health information provided to the user.

25. A method of transacting, as recited in claim 24, wherein the meta-tagging includes semantic meta tagging embedding information into the health information that is relevant thereto and that can be subsequently used to search for certain information or for the purpose of reconciliation.

26. A method of transacting, as recited in claim 24, wherein determining to reconcile and upon determining to reconcile, removing redundant patients or patient medical information from the meta-tagged health information.

27. The method of claim 24 wherein the consolidating includes de-duplicating the relevant health information provided to the user.

28. The method of claim 1 further comprising transforming relevant health information to be provided to the user, wherein the transforming includes mapping from a first coding system to a second coding system.

29. A method of transacting, as recited in claim 1, wherein the probabilistic associations include negative interaction.

30. The method of claim 1 wherein the relevancy of apixions are ranked using a Concept Proximity Model (CPM), and wherein multidimensional conceptual relationships are represented by a set of granular tables that are configured to grow over time.

31. A medical information navigation engine (MINE) configured to transact health information, the MINE comprising:
a processor configured to:
meta-tag health information in response to a health information request (HIR) from a user by associating the health information's content with medical concepts using a relevancy matrix with rows and columns, wherein the relevancy matrix provides probabilistic associations between medical concepts, lab procedures, physiological measurements, medications and allergies, wherein the elements in the rows and columns of the relevancy matrix are apixions, and wherein the HIR is a text query;

search the health information and the meta tags for the apixions matching terms in the text query to identify relevant health information; and provide the relevant health information to the user based upon the user's role, wherein different user roles receive different relevant health information.

32. The MINE of claim 31 further configured to use the apixions to identify different data instances for reconciliation purposes or to identify similar data instances for comparison purposes.

33. The MINE of claim 31 further configured to consolidate the relevant health information provided to the user.

34. The MINE of claim 33 wherein the consolidating includes de-duplicating the relevant health information provided to the user.

35. The MINE of claim 31 wherein the relevancy of apixions are ranked using a Concept Proximity Model (CPM), and wherein multidimensional conceptual relationships are represented by a set of granular tables that are configured to grow over time.

* * * * *